(12) United States Patent
Aran Perramon et al.

(10) Patent No.: US 9,339,518 B2
(45) Date of Patent: May 17, 2016

(54) GENETICALLY MODIFIED MESENCHYMAL STEM CELLS EXPRESSING SST2 FOR THE TREATMENT OF AIRWAY IMMUNE INFLAMMATORY AND LUNG DISEASE

(71) Applicants: Fundacio Institut D'Investigacio Biomedica De Bellvitge (IDIBELL), L'Hospitalet de Llobregat (ES); Ciber Enfermedades Respiratorias, Bunyola (ES); Fundacio Institut De Recerca Hospital Universitari Vall D'Hebron, Barcelona (ES)

(72) Inventors: Josep Maria Aran Perramon, L'Hospitalet de Llobregat (ES); Maria Jesus Cruz Carmona, Barcelona (ES); Itziar Martinez Gonzalez, L'Hospitalet de Llobregat (ES); Oriol Roca Gas, Barcelona (ES); Joan Ramon Masclans Enviz, Bunyola (ES); Javier Munoz Gall, Bunyola (ES)

(73) Assignees: Fundacio Institut D'Investigacio Biomedica De Bellvitge (IDIBELL), L'Hospitalet de Llobregat (ES); Ciber Enfermedades Respiratorias, Bunyola (ES); Fundacio Institut De Recerca Hospital Universitari Vall D'Hebron, Barcelona (ES)

( * ) Notice: Subject to any disclaimer, the term of this patent is extended or adjusted under 35 U.S.C. 154(b) by 0 days.

(21) Appl. No.: 14/359,850

(22) PCT Filed: Nov. 23, 2012

(86) PCT No.: PCT/ES2012/070823
§ 371 (c)(1),
(2) Date: May 21, 2014

(87) PCT Pub. No.: WO2013/076344
PCT Pub. Date: May 30, 2013

(65) Prior Publication Data
US 2014/0315298 A1 Oct. 23, 2014

(30) Foreign Application Priority Data
Nov. 24, 2011 (EP) .................................. 11382362

(51) Int. Cl.
C12N 5/00 (2006.01)
A61K 35/28 (2015.01)
C07K 14/715 (2006.01)
C12N 5/0775 (2010.01)

(52) U.S. Cl.
CPC ............. *A61K 35/28* (2013.01); *C07K 14/7155* (2013.01); *C12N 5/0667* (2013.01); *C12N 2510/00* (2013.01)

(58) Field of Classification Search
USPC ........................................ 435/325; 424/93.21
See application file for complete search history.

(56) References Cited

U.S. PATENT DOCUMENTS

| 2008/0050349 A1* | 2/2008 | Stewart ...................... 424/93.21 |
| 2011/0165128 A1* | 7/2011 | Doronin et al. .............. 424/93.7 |
| 2012/0219572 A1* | 8/2012 | Prockop et al. ............ 424/184.1 |

FOREIGN PATENT DOCUMENTS

| WO | 2010/123942 A2 | 10/2010 |
| WO | 2011/047345 A2 | 4/2011 |

OTHER PUBLICATIONS

Yin (Clin. & Exp. Immunol., May 1, 2011, vol. 164, No. 2, p. 248-255).*
Loebinger (Proc Am Thorac Soc, 2008, vol. 5, p. 711-716.*
Ortiz (PNAS, Jul. 8, 2003, vol. 100, No. 14, p. 8407-8411).*
Raicevic (Human Immunol., 2010, vol. 71, p. 235-244).*
H. Yin et al., "Adenovirus-mediated overexpression of soluble ST2 provides a protective effect on lipopolysaccharide-induced acute lung injury in mice," Clinical & Experimental Immunology, 2011, vol. 164, No. 2, pp. 248-255.
Mauricio Rojas et al., "Bone Marrow-Derived Mesenchymal Stem Cells in Repair of the Injured Lung," American Journal of Respiratory Cell and Molecular Biology, 2005, vol. 33, No. 2, pp. 145-152.
Rafael Moreno et al., "The Beta-Interferon Scaffold Attachment Region Confers High-Level Transgene Expression and Avoids Extinction by Epigenetic Modifications of Integrated Provirus in Adipose Tissue-Derived Human Mesenchymal Stem Cells," Tissue Engineering: Part C, 2011, vol. 17, No. 3, pp. 275-287.
Hiroko Hayakawa et al., "Soluble ST2 Blocks Interleukin-33 Signaling in Allergic Airway Inflammation," Journal of Biological Chemistry, Sep. 2007, vol. 282, No. 36, pp. 26369-26380.
Matthew J. Sweet et al., "A Novel Pathway Regulation Lipopolysaccharide-Induced Shock by ST2/T1 Via Inhibition of Toll-Like Receptor 4 Expression," Journal of Immunology, 2001, vol. 166, No. 11, pp. 6633-6639.
D. E. Smith, "IL-33: a tissue derived cytokine pathway involved in allergic inflammation and asthma," Clinical & Experimental Allergy, 2010, vol. 40, No. 2, pp. 200-208.
International Search Report of PCT/ES2012/070823 dated Feb. 28, 2013.

* cited by examiner

*Primary Examiner* — Michael Wilson
(74) *Attorney, Agent, or Firm* — Sughrue Mion, PLLC

(57) ABSTRACT

The present invention relates to mesenchymal stem cells (MSC) genetically modified to express sST2 or parts thereof for use in the treatment of airway immune inflammatory and lung diseases, wherein said mesenchymal stem cells are not human embryonic stem cells. The present invention also relates to pharmaceutical compositions comprising said mesenchymal stem cells.

8 Claims, 20 Drawing Sheets

A

B

SEQUENCE LISTING

<160> NUMBER OF SEQ ID NOS: 12

<210> SEQ ID NO 1
<211> LENGTH: 328
<212> TYPE: PRT
<213> ORGANISM: Homo sapiens

<400> SEQUENCE: 1

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn

```
                    115                 120                 125
Ser Lys Ile Tyr Cys Pro Thr Ile Asp Leu Tyr Asn Trp Thr Ala Pro
130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325

<210> SEQ ID NO 2
<211> LENGTH: 2542
<212> TYPE: DNA
<213> ORGANISM: Homo sapiens

<400> SEQUENCE: 2
gaggagggac ctacaaagac tggaaactat tcttagctcc gtcactgact ccaagttcat      60
cccctctgtc tttcagtttg gttgagatat aggctactct cccaactca gtcttgaaga     120 gtatcaccaa ctgcctcatg tgtggtgacc ttcactgtcg tatgccagtg actcatctgg     180
agtaatctca caacgagtt accaatactt gctcttgatt gataaacaga tgggttttt     240 ggatcttagc aattctcaca attctcatgt attccacagc agcaaagttt agtaaacaat     300
catggggcct ggaaaatgag gctttaattg taagatgtcc tagacaagga aaacctagtt     360
acaccgtgga ttggtattac tcacaaacaa acaaaagtat tcccactcag gaaagaaatc     420
gtgtgtttgc ctcaggccaa cttctgaagt ttctaccagc tgcagttgct gattctggta     480
tttatacctg tattgtcaga agtcccacat tcaataggac tggatatgcg aatgtcacca     540
tatataaaaa acaatcagat tgcaatgttc cagattattt gatgtattca acagtatctg     600
gatcagaaaa aaattccaaa atttattgtc ctaccattga cctctacaac tggacagcac     660 ctctgagtg gtttaagaat tgtcaggctc ttcaaggatc aaggtacagg gcgcacaagt     720
catttttggt cattgataat gtgatgactg aggacgcagg tgattacacc tgtaaattta     780
tacacaatga aaatggagcc aattatagtg tgacggcgac caggtccttc acggtcaagg     840
atgagcaagg cttttctctg tttccagtaa tcggagcccc tgcacaaaat gaaataaagg     900
```

| | |
|---|---|
| aagtggaaat tggaaaaaac gcaaacctaa cttgctctgc ttgttttgga aaaggcactc | 960 |
| agttcttggc tgccgtcctg tggcagctta atggaacaaa aattacagac tttggtgaac | 1020 |
| caagaattca acaagaggaa gggcaaaatc aaagtttcag caatgggctg gcttgtctag | 1080 |
| acatggtttt aagaatagct gacgtgaagg aagaggattt attgctgcag tacgactgtc | 1140 |
| tggccctgaa tttgcatggc ttgagaaggc acaccgtaag actaagtagg aaaaatccaa | 1200 |
| gtaaggagtg tttctgagac tttgatcacc tgaactttct ctagcaagtg taagcagaat | 1260 |
| ggagtgtggt tccaagagat ccatcaagac aatgggaatg gcctgtgcca taaaatgtgc | 1320 |
| ttctcttctt cgggatgttg tttgctgtct gatctttgta gactgttcct gtttgctggg | 1380 |
| agcttctctg ctgcttaaat tgttcgtcct cccccactcc ctcctatcgt tggtttgtct | 1440 |
| agaacactca gctgcttctt tggtcatcct tgttttctaa cttatgaac tccctctgtg | 1500 |
| tcactgtatg tgaaaggaaa tgcaccaaca accgtaaact gaacgtgttc ttttgtgctc | 1560 |
| ttttataact tgcattacat gttgtaagca tggtccgttc tatacctttt tctggtcata | 1620 |
| atgaacactc attttgttag cgagggtggt aaagtgaaca aaaagggga gtatcaaact | 1680 |
| actgccattt cagtgagaaa atcctaggtg ctactttata ataagacatt tgttaggcca | 1740 |
| ttcttgcatt gatataaaga aatacctgag actgggtgat ttatatgaaa agaggtttaa | 1800 |
| ttggctcaca gttctgcagg ctgtatggga agcatggcgg catctgcttc tggggacacc | 1860 |
| tcaggagctt tactcatggc agaaggcaaa gcaaggcag gcacttcaca cagtaaaagc | 1920 |
| aggagcgaga gagaggtgcc acactgaaac agccagatct catgagaagt cactcactat | 1980 |
| tgcaaggaca gcatcaaaga gatggtgcta aaccattcat gatgaactca cccccatgat | 2040 |
| ccaatcacct cccaccaggc tccacctcga atactgggga ttaccattca gcatgagatt | 2100 |
| tgggcaggaa cacagaccca aaccatacca cacacattat cattgttaaa ctttgtaaag | 2160 |
| tatttaaggt acatggaaca cacgggaagt ctggtagctc agcccatttc tttattgcat | 2220 |
| ctgttattca ccatgtaatt caggtaccac gtattccagg gagccttttct tggccctcag | 2280 |
| tttgcagtat acacactttc caagtactct tgtagcatcc tgtttgtatc atagcactgg | 2340 |
| tcacattgcc ttacctaaat ctgtttgaca gtctgctcaa cacgactgca agctccatga | 2400 |
| gggcagggac atcatctctt ccatctttgg gtccttagtg caatacctgg cagctagcca | 2460 |
| gtgctcagct aaatatttgt tgactgaata aatgaatgca caaccaaaaa aaaaaaaaa | 2520 |
| aaaaaaaaaa aaaaaaaaaa aa | 2542 |

<210> SEQ ID NO 3
<211> LENGTH: 337
<212> TYPE: PRT
<213> ORGANISM: Mus musculus

<400> SEQUENCE: 3

Met Ile Asp Arg Gln Arg Met Gly Leu Trp Ala Leu Ala Ile Leu Thr
1               5                   10                  15

Leu Pro Met Tyr Leu Thr Val Thr Glu Gly Ser Lys Ser Ser Trp Gly
            20                  25                  30

Leu Glu Asn Glu Ala Leu Ile Val Arg Cys Pro Gln Arg Gly Arg Ser
        35                  40                  45

Thr Tyr Pro Val Glu Trp Tyr Tyr Ser Asp Thr Asn Glu Ser Ile Pro
    50                  55                  60

Thr Gln Lys Arg Asn Arg Ile Phe Val Ser Arg Asp Arg Leu Lys Phe
65                  70                  75                  80

```
Leu Pro Ala Arg Val Glu Asp Ser Gly Ile Tyr Ala Cys Val Ile Arg
             85                  90                  95

Ser Pro Asn Leu Asn Lys Thr Gly Tyr Leu Asn Val Thr Ile His Lys
            100                 105                 110

Lys Pro Ser Cys Asn Ile Pro Asp Tyr Leu Met Tyr Ser Thr Val
        115                 120                 125

Arg Gly Ser Asp Lys Asn Phe Lys Ile Thr Cys Pro Thr Ile Asp Leu
        130                 135                 140

Tyr Asn Trp Thr Ala Pro Val Gln Trp Phe Lys Asn Cys Lys Ala Leu
145                 150                 155                 160

Gln Glu Pro Arg Phe Arg Ala His Arg Ser Tyr Leu Phe Ile Asp Asn
                165                 170                 175

Val Thr His Asp Asp Glu Gly Asp Tyr Thr Cys Gln Phe Thr His Ala
            180                 185                 190

Glu Asn Gly Thr Asn Tyr Ile Val Thr Ala Thr Arg Ser Phe Thr Val
            195                 200                 205

Glu Glu Lys Gly Phe Ser Met Phe Pro Val Ile Thr Asn Pro Pro Tyr
        210                 215                 220

Asn His Thr Met Glu Val Glu Ile Gly Lys Pro Ala Ser Ile Ala Cys
225                 230                 235                 240

Ser Ala Cys Phe Gly Lys Gly Ser His Phe Leu Ala Asp Val Leu Trp
                245                 250                 255

Gln Ile Asn Lys Thr Val Val Gly Asn Phe Gly Glu Ala Arg Ile Gln
                260                 265                 270

Glu Glu Glu Gly Arg Asn Glu Ser Ser Ser Asn Asp Met Asp Cys Leu
        275                 280                 285

Thr Ser Val Leu Arg Ile Thr Gly Val Thr Glu Lys Asp Leu Ser Leu
        290                 295                 300

Glu Tyr Asp Cys Leu Ala Leu Asn Leu His Gly Met Ile Arg His Thr
305                 310                 315                 320

Ile Arg Leu Arg Arg Lys Gln Pro Ser Lys Glu Cys Pro Ser His Ile
                325                 330                 335

Ala

<210> SEQ ID NO 4
<211> LENGTH: 3002
<212> TYPE: DNA
<213> ORGANISM: Mus musculus

<400> SEQUENCE: 4
agtgagacag cagcattttt gaacaagtca tggattttgg ctaaaactaa aattctatga      60
tgggcgggtt aaaaaaaaat gccaagacat ctgtgtattt aaaaagaaag agggagcatg     120
cccacgtggg tcgtctgcag aaatgagacg aaggagcgcc aagtagcctc acggtctgta     180
gcttattctc tccagccctt catctgggta tctacagtga tttctcttct ggacccatc      240 tcagagagca cttgtcaacc gcctagtgaa cacaccatta ctatcctgtg ccattgccat     300
agagagacct cagccatcaa tcactagcac atgattgaca dacagagaat gggactttgg     360
gctttggcaa ttctgacact tcccatgtat ttgacagtta cggagggcag taaatcgtcc     420
tggggtctgg aaaatgaggc tttaattgtg agatgccccc aaagaggacg ctcgacttat     480
cctgtggaat ggtattactc agatacaaat gaaagtattc ctactcaaaa aagaaatcgg     540
atctttgtct caagagatcg tctgaagttt ctaccagcca gagtggaaga ctctgggatt     600
tatgcttgtg ttatcagaag ccccaacttg aataagactg gatacttgaa tgtcaccata     660
```

```
cataaaaagc cgccaagctg caatatccct gattatttga tgtactcgac agtacgtgga    720
tcagataaaa atttcaagat aacgtgtcca acaattgacc tgtataattg acagcacct     780 gttcagtggt ttaagaactg caaagctctc caagagccaa ggttcagggc acacaggtcc    840
tacttgttca ttgacaacgt gactcatgat gatgaaggtg actacacttg tcaattcaca    900
cacgcggaga atggaaccaa ctacatcgtg acggccacca gatcattcac agttgaagaa    960
aaaggctttt ctatgtttcc agtaattaca aatcctccat acaaccacac aatggaagtg   1020
gaaataggaa aaccagcaag tattgcctgt tcagcttgct ttggcaaagg ctctcacttc   1080
ttggctgatg tcctgtggca gattaacaaa acagtagttg aaattttgg tgaagcaaga    1140 attcaagaag aggaaggtcg aaatgaaagt ccagcaatg acatggattg tttaacctca    1200
gtgttaagga taactggtgt gacagaaaag gacctgtccc tggaatatga ctgtctggcc   1260
ctgaaccttc atggcatgat aaggcacacc ataaggctga aaggaaaca accaagtaag    1320 gagtgtccct cacacattgc ttgaataaat tggctgaatc agctgtgcac tgcatccgtt   1380
ttctccgagg actgtgtgtt gtagcttggt cccagggaat ccatcatgat caagggaata   1440
gttggcctgt tcatcaagt gttcttctca cgttgaggaa gctccttaaa tctggtctt    1500 ccagaatgtt tctgtcttcc aacaggaatc tctgtcattg tatccttccc ctctctgtgt   1560
cccctcctcc ttgttctccc cgcagtcctc cccatctcct cacctccctt aatgtgttct   1620
tgaccccctt ctctcttttc cttctctctg agctccttct cacccaatag tggcttttgc   1680
agtcatcctt gtaccgact acaagggaca ttggtattgg tagtgggttc agagcagtaa    1740
taactctgct gtgtctcttt gtataacctt gtcatggaaa acaacttaca aactttcatt   1800
ctgagcagtt attaattccc ttgcttggtc ctgggttga caggtgcagc catcatgata    1860
gatagatgac caacctgatc cgattttaaa agagtaaaca tcttttttac ccttatcact   1920
ctcttatgat actgaccact gccttactgg caatacaact aatatgaaaa cattttaat   1980 ttctttcaaa tatcaagagg gcatgggagg gagagagaca ctaactctaa gatcatagca   2040
atatgtgggg catttatttg gatgaatata ttgattaaaa gggtagggtg gaggtaccta   2100
ttagattcag tcatgctgtg tctctgcctg aagtggtatt tgggattttt gttgattctg   2160
tttgtcttct tttgtttgtt ttactatag aaactattct gcccttgtac tcctagagtc    2220
acctgtcttt gcctcccagt tactgggact aaagctatgt gtcaccttac tgagccaggg   2280
tgtttcttgt tttggttttg attttagagc ctctggcttg taacattttt ataaaacaga   2340
attttgattc ctaggtggcc agagttgtga ctcatagagg gattttgtg ctgttgtgat    2400 cagtgaggtc ttggggatct gccctgata atggtgttac tccgggtgac tgtggaccac    2460
agcactgtgt tccagatgg tggtggtcac tgcacattct gcaggaaaag gaatccaaa    2520 cccctattct cacccagttt gaccttgatt ccacaatgcc ttcctctgta acaggatctt   2580
ttgtctagat ttctgagtgt actttagttc acgtttgtat tagaattata tttttttaatc   2640 agtaattttg tatttgtttt gtttgtgtgt gatttctttg ttttccagtt tatttttaat    2700
tcacttgttg ctattcaaat caatgtgttc atactgtttg aacaacacag cgtattaaat    2760
aaaattcgtg tctattgttc ttgaatgatc ataatgaatt cttctgatat tcttaaatt    2820 ataaaatcaa aaaccttata aagcctccct ctgtatttct caacaccact aggtacaagt   2880
agagtgtctg tgataacaat aattcatatt catgttcaat gttttctatg ttgaagccag   2940
atgtcttcaa catatgtctt agaatttctc atttatctttt ttaccccata ctatttgtca   3000
```

| at | 3002 |

<210> SEQ ID NO 5
<211> LENGTH: 20
<212> TYPE: DNA
<213> ORGANISM: Artificial Sequence
<220> FEATURE:
<223> OTHER INFORMATION: Primer ST2 forward from 5' to 3'

<400> SEQUENCE: 5

| atgattgaca gacagagaat | 20 |

<210> SEQ ID NO 6
<211> LENGTH: 20
<212> TYPE: DNA
<213> ORGANISM: Artificial Sequence
<220> FEATURE:
<223> OTHER INFORMATION: Primer ST2 Reverse from 5' to 3'

<400> SEQUENCE: 6

| agcaatgtgt gagggacact | 20 |

<210> SEQ ID NO 7
<211> LENGTH: 21
<212> TYPE: DNA
<213> ORGANISM: Artificial Sequence
<220> FEATURE:
<223> OTHER INFORMATION: Primer seqST2 forward from 5' to 3'

<400> SEQUENCE: 7

| cacaggtcct acttgttcat t | 21 |

<210> SEQ ID NO 8
<211> LENGTH: 20
<212> TYPE: DNA
<213> ORGANISM: Artificial Sequence
<220> FEATURE:
<223> OTHER INFORMATION: Primer seqST2 reverse from 5' to 3'

<400> SEQUENCE: 8

| gttggttcca ttctccgcgt | 20 |

<210> SEQ ID NO 9
<211> LENGTH: 74
<212> TYPE: DNA
<213> ORGANISM: Artificial Sequence
<220> FEATURE:
<223> OTHER INFORMATION: Primer Adv-ST2 forward from 5' to 3'

<400> SEQUENCE: 9

| tcggcgcacg ctggaagacg cggaggctct cttcagtaaa tactgcgatg attgacagac | 60 |
| agagaatggg actt | 74 |

<210> SEQ ID NO 10
<211> LENGTH: 100
<212> TYPE: DNA
<213> ORGANISM: Artificial Sequence
<220> FEATURE:
<223> OTHER INFORMATION: Primer 2A-FLAG-ST2 reverse from 5' to 3'

<400> SEQUENCE: 10

| gctttaacag agagaagttc gtggctccgg accctctaga cttatcgtcg tcatccttgt | 60 |
| aatcatacga gtcagcaatg tgtgagggac actccttact | 100 |

```
<210> SEQ ID NO 11
<211> LENGTH: 43
<212> TYPE: DNA
<213> ORGANISM: Artificial Sequence
<220> FEATURE:
<223> OTHER INFORMATION: Primer pWPT-BamHI-ST2 forward from 5' to 3'

<400> SEQUENCE: 11
gtcgtgacgc ggatccatga ttgacagaca gagaatggga ctt                 43

<210> SEQ ID NO 12
<211> LENGTH: 40
<212> TYPE: DNA
<213> ORGANISM: Artificial Sequence
<220> FEATURE:
<223> OTHER INFORMATION: Primer pWPT-SalI-EGFP reverse from 5' to 3'

<400> SEQUENCE: 12
ggaattccct cgaggtcgac ttacttgtac gctcgtccat                     40
```

GENETICALLY MODIFIED MESENCHYMAL STEM CELLS EXPRESSING SST2 FOR THE TREATMENT OF AIRWAY IMMUNE INFLAMMATORY AND LUNG DISEASE

CROSS REFERENCE TO RELATED APPLICATIONS

This is a National Stage of International Application No. PCT/ES2012/070823 filed Nov. 23, 2012, claiming priority based on European Patent Application No. 11382362.9 filed Nov. 24, 2011, the contents of all of which are incorporated herein by reference in their entirety.

FIELD OF THE INVENTION

The present invention relates to the field of engineered stem cells and their therapeutic use.

BACKGROUND OF THE INVENTION

The acute lung injury (also known as ALI) and acute respiratory distress syndrome (also known as ARDS and representing the more severe expression of ALI) are associated with diffuse cellular infiltration and proteinacious edema (Ware L B. The ARSD. NEJM 2000; 34: 660-1). This fact is a reflection of a significant lung inflammatory state, with activation of humoral and cellular mediators causing changes in lung architecture itself, which induce serious disturbances in pulmonary gas exchange. ALI/ARDS may be due from both intra-pulmonary (bacterial or viral pneumonia, aspiration, inhalation of gases, graft dysfunction in lung transplant, cystic fibrosis, . . . ) and extra-pulmonary processes (sepsis, pancreatitis, polytransfusion, etc), but the more frequent cause is bacterial pneumonia.

Substantial progress has been made in reducing mortality and morbidity from ALI and the ARDS with improved supportive care, specifically lung-protective ventilation and a fluid-conservative strategy. However, morbidity and mortality remains unacceptably high. In fact, ALI is responsible for up to 75,000 deaths and 3.6 million hospital days in the United States each year (Rubenfeld G O. Incidence and outcome of ALI. NEJM 2005; 353: 1685-93). These data demonstrate that it has a substantial impact on public health. Furthermore, pharmacologic therapies have not been successful in improving outcomes.

Another lung disease involved in the present invention is Chronic Obstructive Pulmonary Disease (COPD), which is defined according to the Global Initiative for Chronic Obstructive Lung Disease (GOLD) as a persistent airflow limitation, which is usually progressive and associated with an abnormal inflammatory response of the lung to noxious particles or gases (Rabe K F et al. GOLD executive summary. Am J Respir Crit Care Med 2007; 176:532-555). The pathogenesis of COPD is characterized by an up-regulation of inflammatory processes leading to irreversible events such as apoptosis of epithelial cells, and proteolysis of the terminal air-space and lung extracellular matrix components. Interestingly, it has some significant extra-pulmonary effects that may contribute to the severity in individual patients. The reality, though, is that COPD is a heterogeneous group of diseases with similar manifestation and includes disparate and overlapping disease processes such as chronic bronchitis, emphysema, asthma, bronchiectasis, and bronchiolitis. The primary cause of COPD is tobacco smoke (including secondhand or passive exposure). However, other risk factors include air pollution, occupational dusts and chemicals, and it could present as a sequelae of lower respiratory infections.

COPD is a leading cause of disability and death. It is a chronic disease that continues to increase in prevalence and mortality, and it is projected to continue to increase into the future (Lopez A D et al. Chronic obstructive pulmonary disease: current burden and future projections. Eur Respir J 2006; 27:397-412). In fact, 80 million people have moderate to severe COPD and more than 3 million people died of COPD in 2005, which corresponds to 5% of all deaths globally (www.who.int). According to new estimates for 2030 by the World Health Organization, COPD is predicted to become the third leading cause of death (www.who.int). Moreover, the burden of COPD is rising, incurring a major health care burden worldwide.

The treatment objectives for COPD include slowing the accelerated decline in lung function; relieving symptoms, such as shortness of breath and cough; improving daily lung function; decreasing exacerbations; and improving quality of life (Pauwels R A, Buist A S, Calverley P M A, Jenkins C R, Hurd S S, on behalf of the GOLD Scientific Committee. Global strategy for the diagnosis, management, and prevention of chronic obstructive pulmonary disease. NHLBI/WHO Global Initiative for Chronic Obstructive Lung Disease (GOLD) workshop summary. Am J Respir Crit Care Med. 2001; 163:1256-1276). While many medications are available to treat COPD, such as bronchodilators and steroids, no drug has demonstrated effectiveness in halting the progression of the disease. Rather, the available pharmacological treatments are essentially symptomatic and the goal of drug therapy at this time is to maintain control of symptoms and to prevent COPD exacerbation. In fact, there is no specific therapy other than smoking cessation in case of smoking-induced emphysema, which is only partially successful in established disease.

Still another lung disease involved in the present invention is asthma. By definition, asthma is a heterogeneous chronic inflammatory disorder of the airways involving an airflow limitation that is at least partly reversible. The condition results in recurrent episodes of wheezing, breathlessness, chest tightness, and cough (Global Initiative for Asthma (GINA)). Global strategy for asthma management and prevention. NIH publication number 95-3659[a]. Bethesda, National Institutes of Health, 1995). Asthma definition includes four domains: variable airway obstruction, airway inflammation, airway hyperresponsiveness, and symptoms, which characterize the underlying disease process.

Perhaps one the most important advances in the treatment of asthma occurred when the inflammatory component of the condition was demonstrated and found to be satisfactorily treated with inhaled corticoids. Early pathological studies in patients with mild asthma who were not treated with corticosteroids reported high eosinophil and lymphocyte counts in the mucosa of the large airways. The number of these cells decreased significantly and the overall lung function improved following administration of high doses of inhaled corticosteroids (Djucanovic R, Wilson J W, Britten K M, Wilson S J, Walls A F, Roche W R, Howarth P H, Holgate S T. Effect of an inhaled corticosteroid on airways inflammation and symptoms in asthma. Am Rev respir Dis 1992; 256: 669-674; Laitinen L A, Laitinen A, Haahtela T. A comparative study of the effects of an inhaled corticosteroid, budesonide, and a beta 2-agonist, terbutaline, on airways inflammation in newly diagnosed asthma: a randomized, double blind, parallel-group controlled trial. J Allergy Clin Immunol 1992; 90:32-42).

Other medications are available to treat asthma, such as bronchodilators. All these treatments are able to reduce inflammation although not totally. Moreover, in some patients, hiperresponsiveness is still present despite the fact that inflammation is reduced, demonstrating that no drug has proven effective to cure the disease.

Still another lung disease involved in the present invention is hypersensitivity pneumonitis. This is a clinical entity characterized by a disintegration of the lung parenchyma and progressive development of pulmonary fibrosis as a result of an immunologic inflammatory response to various antigens after a previous sensitization (Selman M. Hypersensitivity Pneumonitis: a multifaceted deceiving disorder. Clin Chest Med. 2004; 25: 531-547). The progression of the disease leads to chronic respiratory failure due to the development of pulmonary fibrosis established or, in some cases, to chronic obstructive pulmonary disease (COPD), which confers a status of potential severity of this entity (Hanak V, Golbin J M, Ryu J H. Causes and presenting features in 85 consecutive patients with hypersensitivity pneumonitis. Mayo Clin Proc. 2007; 82: 812-816. Selman M, Chapela R, Raghu G. Hypersensitivity pneumonitis: clinical, manifestations, pathogenesis, diagnosis, and therapeutic strategies. Semin Respir Med. 1993; 14: 353-364). In fact, pulmonary fibrosis proved to be a predictor of mortality in these patients, with a mortality of 27% at 5 years and a median survival of 12.8 years (Vourlekis J S, Schwarz M I, Cherniack R M, Curran-Everett D, Cool C D, Tuder R M, King T E, Brown K K. The effect of pulmonary fibrosis on survival in patients with hypersensitivity pneumonitis. Am J Med 2004; 116(10): 662-8.). After inhalation of the antigen, mononuclear infiltrates with a peribronquiovascular distribution are developed (Denis, M., Y. Cormier, and M. Laviolette. 1992. Murine hypersensitivity pneumonitis: a study of cellular infiltrates and cytokine production and its modulation by cyclosporin A. Am. J. Respir. Cell Mol. Biol. 6: 68-74. Denis, M., Y. Cormier, M. Laviolette, and E. Ghadirian. 1992. T cells in hypersensitivity pneumonitis: effects of in vivo depletion of T cells in a mouse model. Am. J. Respir. Cell Mol. Biol. 6: 183-189). These mononuclear infiltrates are composed predominantly of alveolar macrophages and T cells. Th2 cytokines enhance fibrotic processes by activating fibroblast proliferation and collagen production (Mitaka K, Miyazaki Y, Yasui M, Furuie M, Miyake S, Inase N, Yoshizawa Y. Th2-biased Immune responses are important in a murine model of chronic hypersentivity pneumonitis. Int Arch Allergy Immunol 2011; 154: 264-74). Some authors have described TH2-type immune responses in the lesions of usual interstitial pneumonia in patients with hypersensitivity pneumonitis, as has been described in idiopathic pulmonary fibrosis (Kishi M, Miyazaki Y, Jinta T, Furusawa H, Ohtani Y, Inase N, Yoshizawa Y. Pathogenesis of cBFL in common IPF Correlation of IP-10/TARC ratio with histological patterns. Thorax 2008; 63: 810-6) which is a serious entity with a life expectancy of 3.2 to 5 years from diagnosis (Idiopathic Pulmonary Fibrosis: Diagnosis and treatment. International Consensus Statement. Am J Respir Crit Care Med. 2000; 161.646-64; Fernandez Perez E R, Daniels C E, Schroeder D R, St Sauver J, Hartman T E, Bartholmai B J, Yi E S, Ryu J H. Incidence, prevalence, and clinical course of idiophatic pulmonary fibrosis: a population-based study. Chest 2010; 137 (1):129-37).

Thus, in view of the above, there is a need for developing new and more effective therapies for the treatment of airway immune inflammatory and lung diseases. The present inventors have surprisingly found that engineered human mesenchymal stem cells overexpressing the IL-33 decoy receptor sST2 are able to attenuate acute and chronic airway immune inflammatory and lung diseases.

IL-33 is suggested to function as an alarmin that is released upon endothelial and epithelial cell damage. It has recently shown that IL-33 plays a crucial role in innate airway inflammation, but its mechanism of action is still unclear. Indeed, no consensus has been reached whether IL-33 is pro-inflammatory (Oboki et al. (2011) Allergy Asthma Immunol. Res. 3: 81-88) or exerts a protective role in inflammatory states (Miller et al. (2010) Circ. Res. 107: 650-8; Alves-Filho et al. (2010) Nat. Med. 16: 708-12). On the other hand, individuals who did not recover from sepsis, a generalized bacterial infection resulting in widespread inflammation and multiple organ failure, had significantly more sST2 than those who did recover. The present inventors prove herein that the combination of the local and continuous action of both the intrinsic immunomodulatory and anti-inflammatory properties of hMSCs (human mesenchymal stem cells) and the transgenic over-expression of the anti-inflammatory decoy receptor sST2, are able to act synergistically and alleviate the pathological events of acute and chronic airway immune-inflammatory and lung diseases.

The present inventors have demonstrated or shown:

That ASCs (adult stem cells) have lung tropism (good in terms of general safety and therapeutic efficacy to airway and lung diseases).

Selective and persistent (local) sST2 delivery by using ASCs as a continuous sST2 factory (through continuous sST2 over-expression and secretion into the local lung environment).

Synergistic benefits on acute lung injury (ALI), combining the intrinsic immunoregulatory properties of ASCs with the anti-inflammatory action of sST2 as decoy receptor for IL-33.

A profound local anti-inflammatory effect of our cell therapy strategy, reaching both regulatory actions over the cell-mediated, acquired immune response (immunoregulatory action of ASCs, which we demonstrate that are able to induce, among others, anti-inflammatory factors such as COX-2, IDO and TGF-beta). This action is combined with the over-expression of sST2 in these cells by genetic engineering, which acts as decoy receptor for IL-33. This cytokine has been shown to be a crucial amplifier of innate immunity (Oboki et al. (2010) Proc. Natl. Acad. Sci. USA 107: 18581-6). Thus, with our approach, we control both the adaptive and the innate immunity, something which has not been disclosed nor suggested so far. The complete immune response is responsible for the initiation and development of the full inflammatory process occurring in ALI and other lung related pathologies, and the main contributor of airway injury.

Mesenchymal stem cells (MSCs) are multipotent adult stem cells that can be isolated from several sources (bone marrow, cord blood, placenta and adipose tissue) and have the capacity to differentiate into a wide number of cells. MSCs release several growth factors that can regulate endothelial and epithelial permeability, as well as enhance repair. MSCs also release anti-inflammatory cytokines that can dampen the severity of inflammation. Furthermore, MSCs can regulate innate and adaptive immunity by effects on T and B cells, dendritic cells, monocytes, neutrophils, and macrophages.

Based on preclinical studies, MSCs reduce the severity of organ injury as well as enhance recovery (Matthay M A et al. Chest 2010; 138: 965-972). Several experimental studies have shown that MSCs may have potential therapeutic application in clinical disorders, including myocardial infarction, diabetes, hepatic failure, acute renal failure, and sepsis.

On the other hand, a recent review (Smith D E. IL-33: a tissue derived cytokine pathway involved in allergic inflammation and asthma. Clin Exp Allergy. 2010 February; 40(2): 200-8) shows that IL33 is one of the main cytokines that contribute to inflammation in asthma and allergy. In addition, experimental evidence and clinical observations have associated ST2 with immune-inflammatory processes such as asthma (Sweet M J, et al. A novel pathway regulating lipopolysaccharide-induced shock by ST2/T1 via inhibition of Toll-like receptor 4 expression. J Immunol. 2001; 166(11): 6633-9). Moreover, using different models of lung inflammation, it has been postulated a role of sST2 in the attenuation of immune responses mediated by Th2 cells (Hayakawa H, et al. Soluble ST2 blocks interleukin-33 signaling in allergic airway inflammation. J Biol Chem. 2007 Sep. 7; 282(36):26369-80). sST2 acts as a negative regulator of the production of Th2 cytokines (IL-4, IL-5, IL-13), triggering the inflammatory response in asthma, by antagonizing signaling via IL-33 and suppressing the activation of NF-kappaB.

In view of the above, the object of the present invention is to provide a new therapy based on engineered mesenchymal stem cells for use in the treatment of airway immune inflammatory and lung diseases.

A second object of the present invention is to provide a pharmaceutical composition based on mesenchymal stem cells for use in the treatment of airway immune inflammatory and lung diseases.

BRIEF DESCRIPTION OF THE DRAWINGS

(FIG. 2A) Schematic proviral configuration of the pWPTsST2FLAG2AEGFP (pWPT-sST2-EGFP) lentiviral vector employed. The resulting bicistronic transcript contains, in a 5' to 3' orientation, sequences encoding the C-terminus FLAG-tagged murine sST2 gene followed by the picornavirus-derived 2A peptide mediating co-translational cleavage from the second cistron, and the EGFP reporter gene. (FIG. 2B) Left image: pWPT-sST2-EGFP-transduced hASCs express both the sST2 and the EGFP transgenes. sST2 and EGFP protein expression assessed in cell extracts by Western blot. Detection of the specific 64 kD sST2-FLAG band in hASCs transduced with pWPT-sST2-EGFP (lane 2), but not in hASCs transduced with the control counterpart pWPT-EGFP (lane 1), both at a MOI=20. Conversely, the reporter EGFP protein was detected in both pWPT-sST2-EGFP- and pWPT-EGFP-transduced hASCs. Endogenous tubulin expression verified comparable protein loading between lanes. Center image: representative flow cytometry histogram from hASCs transduced with pWPT-sST2-EGFP (MOI=20) showing the transduction efficiency as the percentage of EGFP-positive hASCs (dark profile) respect to the autofluorescent signal from non-transduced hASCs (clear profile). Right image: EGFP expression from pWPT-sST2-EGFP-transduced hASCs (MOI=20) by fluorescence microscopy (×20 magnification). Lower image: sST2 protein expression assessed in cell culture supernatants by ELISA. The levels of murine sST2 were evaluated from supernatants collected 48 h after lentiviral transduction at the indicated MOIs. White columns, pWPT-sST2-EGFP-transduced hASCs; grey column, pWPT-EGFP-transduced hASCs. The sST2 level of NIH3T3 mouse fibroblast supernatants induced with LPS (10 µg/ml) for 48 h were determined for comparison (black column). Data are represented as mean values±SD (n=3).

DESCRIPTION OF THE INVENTION

Figure 1:
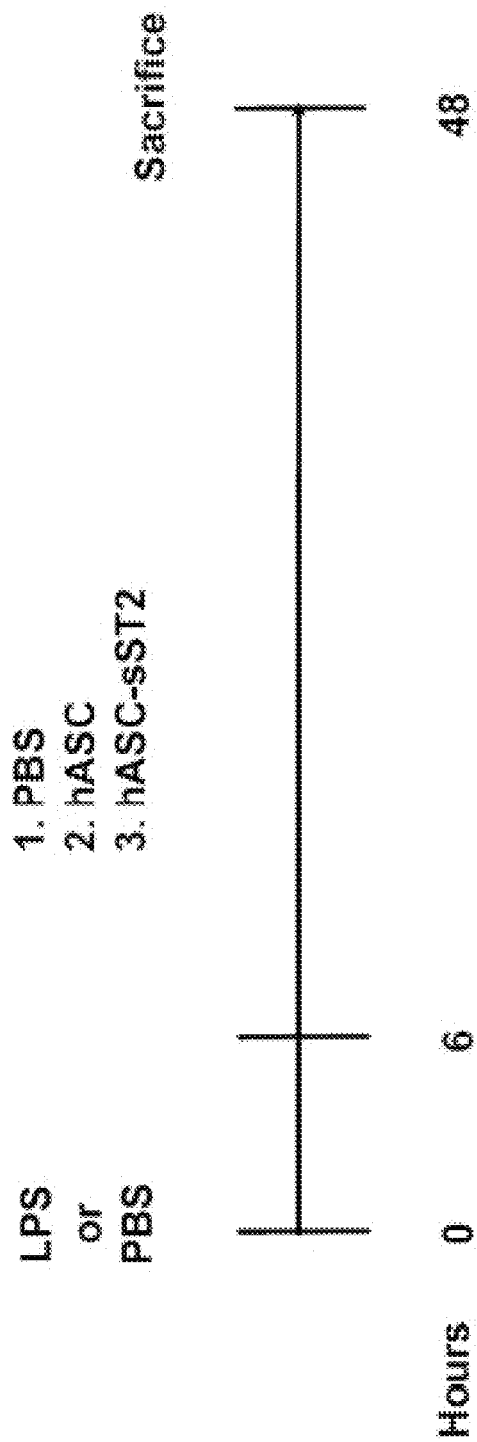
FIG. 1. Experimental design for the in vivo hASC (human adult stem cell) transplantation study. BalB/c mice initially received LPS or PBS by nasal instillation, followed by intravenous injection 6 h later with PBS, genetically engineered hASCs over-expressing EGFP (hASC), or genetically engineered hASCs over-expressing both sST2 and EGFP (hASC-sST2). Mice were then sacrificed 48 h after the initial pathogenic challenge to evaluate the therapeutic efficacy.

In a first aspect, the present invention relates to mesenchymal stem cells (MSC) genetically modified to express sST2 or parts thereof for use in the treatment of airway immune inflammatory and lung diseases, wherein said mesenchymal stem cells are not human embryonic stem cells. The amino acid sequence of sST2 is well known in the art as the soluble or extracellular domain of T1/ST2, and is defined as residues 1-328 of SEQ ID NO: 1 (human), and residues 1-337 of SEQ ID NO: 3 (mouse), and are identified by GenBank Accession No. NP_003847.2 and GenBank Accession No. NP_034873.2, respectively. "variants thereof", when refer herein to sST2, means any variant (fragment, analog or derivative) of mammalian sST2 which maintains the functional activity of wild-type sST2. Such variants include, for example, a polypeptide encoded by a naturally occurring allelic variant of native sST2 gene (i.e., a naturally occurring nucleic acid that encodes a naturally occurring mammalian sST2 polypeptide), a polypeptide encoded by an alternative spliced form of a native sST2 gene, a polypeptide encoded by a homolog or ortholog of a native sST2 gene, and a polypeptide encoded by a non-naturally occurring variant of a native sST2 gene.

sST2 variants according to the present invention have a peptide sequence that differs from a native sST2 polypeptide in one or more amino acids, maintaining the functional activity of wild-type sST2. The peptide sequence of such variants can feature a deletion, addition, or substitution of one or more amino acids of an sST2 variant. Amino acid insertions are preferably of about 1 to 40 contiguous amino acids, and deletions are preferably of about 1 to 10 contiguous amino acids. Variant sST2 polypeptides substantially maintain a native sST2 functional activity. Preferred sST2 polypeptide variants can be made by expressing nucleic acid molecules within the invention that feature silent or conservative changes. sST2 polypeptide fragments corresponding to one or more particular motifs and/or domains or to arbitrary sizes, are within the scope of the present invention. Isolated peptidyl portions of sST2 can be obtained by screening sST2 recombinant peptides produced from the corresponding fragment of the nucleic acid encoding such peptides.

For example, an sST2 polypeptide of the present invention may be arbitrarily divided into fragments of desired length with no overlap of the fragments, or preferably, divided into overlapping fragments of a desired length. The fragments can be produced recombinantly and tested to identify those peptidyl fragments which can function as agonists of native sST2 polypeptides.

Variants of sST2 polypeptides can also include recombinant forms of the sST2 polypeptides. Recombinant polypeptides preferred by the present invention, in addition to the sST2 polypeptide, are encoded by a nucleic acid that can have at least about 70% sequence identity with the nucleic acid sequence of a gene encoding a mammalian sST2 polypeptide. These polypeptides equally maintain the functional activity of wild-type sST2.

sST2 polypeptide variants can include agonistic forms of the protein that constitutively express the functional activities of a native sST2 polypeptide. Other sST2 polypeptide variants can include those that are resistant to proteolytic cleavage, as for example, due to mutations, which alter protease target sequences. Whether a change in the amino acid sequence of a peptide results in a variant having one or more functional activities of a native sST2 polypeptide, this can be readily determined by comparing the functional activity of the variant with the functional activity of a native sST2 polypeptide.

The MSCs according to the present invention can be genetically modified with a nucleic acid that encodes sST2 or a variant of sST2. The nucleic acid can be a native or non-native nucleic acid and be in the form of RNA or in the form of DNA (e.g., cDNA, genomic DNA, and synthetic DNA). The DNA can be double-stranded or single-stranded, and if single-stranded may be the coding (sense) strand or non-coding (antisense) strand. The nucleic acid coding sequence that encodes an sST2 polypeptide may be substantially similar to the nucleotide sequence of an sST2 gene, comprising nucleotides 231 to 1217 of SEQ ID NO: 2 (human), and nucleotides 331 to 1344 of SEQ ID NO: 4 (mouse), which are identified by GenBank Accession No. NM_003856.2 and GenBank Accession No. NM_010743.2, respectively. The nucleic acid coding sequence of sST2 can also be a different coding sequence which, as a result of the redundancy or degeneracy of the genetic code, encodes the same polypeptide as SEQ ID NO: 1 (human) or SEQ ID NO: 3 (mouse).

Other nucleic acid molecules that encode sST2 within the invention are variants of a native sST2 gene, such as those that encode fragments, analogs and derivatives of a native sST2 polypeptide. Such variants may be, for example, a naturally occurring allelic variant of a native sST2 gene, a homolog or ortholog of a native sST2 gene, or a non-naturally occurring variant of a native sST2 gene. These variants have a nucleotide sequence that differs from a native sST2 gene in one or more bases. For example, the nucleotide sequence of such variants can feature a deletion, addition, or substitution of one or more nucleotides of a native sST2 gene. Nucleic acid insertions are preferably of about 1 to 40 contiguous nucleotides, and deletions are preferably of about 1 to 10 contiguous nucleotides.

Variant sST2 polypeptides displaying substantial changes in structure can be generated by making nucleotide substitutions that cause less conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in polypeptide structure are those that cause substitution of (a) a hydrophilic residue (e.g., serine or threonine) for (or by) a hydrophobic residue (e.g., leucine, isoleucine, phenylalanine, valine or alanine) (b) a cysteine or proline for (or by) any other residue; (c) a residue having an electropositive side chain (e.g., lysine, arginine, or histidine) for (or by) an electronegative residue (e.g., glutamine or aspartine); or (d) a residue having a bulky side chain (e.g., phenylalanine) for (or by) one not having a side chain (e.g., glycine).

Naturally occurring allelic variants of a native sST2 gene within the invention are nucleic acids isolated from mammalian tissue that have at least about 70% sequence identity with a native sST2 gene, and encode polypeptides having structural similarity to a native sST2 polypeptide and maintain the functional activity of wild-type sST2. Homologs of a native sST2 gene within the invention are nucleic acids isolated from other species that have at least about 70% sequence identity with the native gene, and encode polypeptides having structural similarity to a native sST2 polypeptide. Public and/or proprietary nucleic acid databases can be searched to identify other nucleic acid molecules having a high percent (e.g., 70% or more) sequence identity to a native sST2 gene.

Non-naturally occurring sST2 gene variants are nucleic acids that do not occur in nature (e.g., are made by the hand of man), have at least about 70% sequence identity with a native sST2 gene, and encode polypeptides having structural similarity to a native sST2 polypeptide and maintain the functional activity of wild-type sST2. Examples of non-naturally occurring sST2 gene variants are those that encode a fragment of a native sST2 protein, those that hybridize to a native sST2 gene or a complement of native sST2 gene under stringent conditions, and those that share at least 65% sequence identity with a native sST2 gene or a complement of a native sST2 gene.

Nucleic acids encoding fragments of a native sST2 gene within the invention are those that encode amino acid residues of a native sST2 polypeptide and therefore maintain the functional activity of wild-type sST2. Shorter oligonucleotides that encode or hybridize with nucleic acids that encode fragments of a native sST2 polypeptide can be used as probes, primers, or antisense molecules. Longer polynucleotides that encode or hybridize with nucleic acids that encode fragments of a native sST2 polypeptide can also be used in various aspects of the invention. Nucleic acids encoding fragments of a native sST2 can be made by enzymatic digestion (e.g., using a restriction enzyme) or chemical degradation of the full length native sST2 gene or variants thereof.

Nucleic acids that hybridize under stringent conditions to one of the foregoing nucleic acids can also be used in the invention. For example, such nucleic acids can be those that hybridize to one of the foregoing nucleic acids under low stringency conditions, moderate stringency conditions, or high stringency conditions are within the invention. Nucleic acid molecules encoding an sST2 fusion protein may also be used in the invention. Such nucleic acids can be made by preparing a construct (e.g., an expression vector) that expresses an sST2 fusion protein when introduced into a suitable target cell. For example, such a construct can be made by ligating a first polynucleotide encoding an sST2 protein fused in frame with a second polynucleotide encoding another protein such that expression of the construct in a suitable expression system yields a fusion protein. Said nucleic acid molecule encoding an sST2 fusion protein can also be a molecule coding for a carboxy- or amino-terminal fusion protein consisting of sST2 and an optimized export signal able to improve its release from mesenchymal stem cells, able to improve its traceability (GFP reporter, FLAG or other tags, . . . ).

The nucleic acids used to over-express sST2 can be modified at the base moiety, sugar moiety, or phosphate backbone, for example, to improve stability of the molecule, hybridization, etc. The nucleic acids within the invention may additionally include other appended groups such as peptides (e.g., for targeting target cell receptors in vivo), or agents facilitating transport across the cell membrane, or hybridization-triggered cleavage. To this end, the nucleic acids may be conjugated to another molecule (e.g., a peptide, hybridization triggered crosslinking agent, transport agent, hybridization-triggered cleavage agent, etc).

The sST2 can be over-expressed from the MSCs by introducing an agent into the stem cells, during, for example, culturing of the MSCs, MAPCs, and/or other stem cells that promote expression of sST2. The agent can comprise natural or synthetic nucleic acids (e.g., exogenous genetic material), according to present invention and described above, that are incorporated into recombinant nucleic acid constructs, typically DNA constructs, capable of introduction into and replication in the cell. Such a construct preferably includes a replication system and sequences that are capable of transcription and translation of a polypeptide-encoding sequence in a given target cell. Other agents can also be introduced into the MSCs to promote expression of sST2 from the stem cells. For example, agents that increase the transcription of a gene encoding sST2, increase the translation of an mRNA encoding sST2, and/or those that decrease the degradation of an mRNA encoding sST2 could be used to increase sST2 levels. Increasing the rate of transcription from a gene within a cell can be accomplished by introducing an exogenous promoter upstream of the gene encoding sST2. Enhancer elements, which facilitate expression of a heterologous gene, may also be employed.

A preferred method of introducing the agent into a MSC involves using gene therapy. Gene therapy refers to gene transfer to express a therapeutic product from a cell in vivo, ex vivo, or in vitro. Gene therapy in accordance with the present invention can be used to express sST2 from the MSC in vivo, ex vivo, and/or in vitro. One method of gene therapy uses a vector including a nucleotide encoding an sST2. A "vector" (sometimes referred to as gene delivery or gene transfer "vehicle") refers to a macromolecule or complex of molecules comprising a polynucleotide to be delivered to a target cell, either in vitro or in vivo. The polynucleotide to be delivered may comprise a coding sequence of interest in gene therapy. Therefore, the MSC of the present invention may comprise a vector containing nucleic acids that encode the expression of sST2 or variants thereof with functional activity of wild-type sST2. Vectors may include, but not limited to, non-viral vectors (plasmid, . . . ), viral (retroviral, lentiviral, adeno-associated, adenoviral, . . . ),
liposomes and other lipid-containing complexes, and other macromolecular complexes capable of mediating delivery of a polynucleotide to a target cell, able to improve the expression levels of the sST2 protein or sST2 protein fusion.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors, which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors that can be used in the present invention include viral vectors, lipid based vectors and other vectors that are capable of delivering a polynucleotide according to the present invention to the MSCs. The vector can be a targeted vector, especially a targeted vector that preferentially binds to MSCs. Preferred viral vectors for use in the invention are those that exhibit low toxicity to a target cell and induce production of therapeutically useful quantities of sST2.

One example of a viral vector that can be used to genetically modify MSCs is a retrovirus. The use of retroviruses for genetically modifying MSCs is disclosed in U.S. Pat. No. 5,591,625. The structure and life cycle of retroviruses makes them ideally suited to be gene-transfer vehicles since (i) the majority of sequences coding for their structural genes are deleted and replaced by the gene(s) of interest, which are transcribed under control of the retroviral regulatory sequences within its long terminal repeat (LTR) region and (ii) they replicate through a DNA intermediate that integrates into the host genome. Although the sites of integration appear to be random with respect to the host genome, the provirus integrates with a defined structure in low copy number.

Retroviruses can be RNA viruses; i.e., the viral genome is RNA. This genomic RNA is, however, reverse transcribed into a DNA intermediate which is integrated very efficiently into the chromosomal DNA of infected cells. This integrated DNA intermediate is referred to as a provirus. The retroviral genome and the proviral DNA have three genes: the gag, the pol and the env, which are flanked by two long terminal repeat (LTR) sequences. The gag gene encodes the internal structural (nucleocapsid) proteins, the pol gene encodes the RNA-directed DNA polymerase (reverse transcriptase); and the env gene encodes viral envelope glycoproteins. The 5' and 3'LTRs serve to promote transcription and polyadenylation of virion RNAs.

Adjacent to the 5' LTR are sequences necessary for reverse transcription of the genome (the tRNA primer binding site) and for efficient encapsidation of viral RNA into particles (the Psi site). Mulligan, R. C., In: Experimental Manipulation of Gene Expression, M. Inouye (ed). Proceedings of the National Academy of Sciences, U.S.A. 81: 6349-6353 (1984).

In order to generate a viral particle containing the recombinant genome, it is necessary to develop cell lines that provide packaging "help". To accomplish this, a plasmid(s), encoding, for example, the retroviral structural genes gag, pol, and env, is introduced into an otherwise untransformed tissue cell line by conventional calcium-phosphate mediated DNA transfection (Wigler, et al., Cell 11:223 (1977)). These plasmid-containing cells are referred to as a "packaging cell line." These plasmid containing packaging cell lines can be maintained as such or a replication incompetent retroviral vector can be introduced into the cell's genome. In the latter case, the genomic RNA generated by the vector construct combines with the constitutively expressed retroviral structural proteins of the packaging line, resulting in the release of retroviral particles into the culture medium. A stable cell line containing the structural gene sequences of the retroviruses is a retroviral "producer cell line."

Because genes can be introduced into MSCs using a retroviral vector, they can be "on" (subject to) the retroviral vector control; in such a case, the gene of interest is transcribed from a retroviral promoter. A promoter is a specific nucleotide sequence recognized by RNA polymerase molecules that start RNA synthesis. Alternatively, retroviral vectors having additional promoter elements (in addition to the promoter incorporated in the recombinant retrovirus), which are responsible for the transcription of the genetic material of interest, can be used. For example, a construct in which there is an additional promoter modulated by an external factor or cue can be used, making it possible to control the level of polypeptides being produced by the MSCs by activating that external factor of cue. For example, heat shock proteins are proteins encoded by genes in which the promoter is regulated by temperature. The promoter of the gene, which encodes the metal-containing protein metallothioneine, is responsive to cadmium (Cd++) ions. Incorporation of this promoter or another promoter influenced by external cues also makes it possible to regulate the production of the polypeptide by the engineered progenitor cells.

Examples of vectors other than retroviruses that can be used to genetically engineer or modify MSCs can be derived from adenovirus (Ad) or adeno-associated virus (AAV). Both human and nonhuman viral vectors can be used, but preferably the recombinant viral vector is replication-defective in humans. Where the vector is an adenovirus, it preferably comprises a polynucleotide having a promoter operably linked to a gene encoding sST2 and is replication-defective in humans.

Adenovirus vectors are capable of highly efficient gene expression in target cells and can accommodate a relatively large amount of heterologous (non-viral) DNA. A preferred form of recombinant adenovirus is a "gutless, "high-capacity", or "helper-dependent" adenovirus vector. Such a vector features, for example, (1) the deletion of all or most viral-coding sequences (those sequences encoding viral proteins), (2) the viral inverted terminal repeats (ITRs) which are sequences required for viral DNA replication, (3) up to 28-32 kb of "exogenous" or "heterologous" sequences (e.g., sequences encoding sST2), and (4) the viral DNA packaging sequence which is required for packaging of the viral genomes into infectious capsids. For specifically epithelial, endothelial or mesenchymal cells, preferred variants of such recombinant adenoviral vectors contain tissue-specific (e.g., MSCs) enhancers and promoters operably linked to an sST2 gene.

AAV-based vectors are advantageous because they exhibit high transduction efficiency of target cells and can integrate into the target genome in a site-specific manner. Use of recombinant AAV vectors is discussed in detail in Tal, J., J. Biomed. Sci. 7:279-291, 2000 and Monahan and Samulski, Gene Therapy 7:24-30, 2000. A preferred AAV vector comprises a pair of AAV inverted terminal repeats (ITRs), which flank at least one cassette containing a tissue or cell specific promoter operably linked to an sST2 nucleic acid. The DNA sequence of the AAV vector, including the ITRs, the promoter and the sST2 gene may be integrated into the target genome.

Other viral vectors that can be used in accordance with the present invention include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid. A preferred HSV vector is one that: (1) is engineered from HSV type I, (2) has its IE genes deleted, and (3) contains a tissue-specific (e.g., epithelium, endothelium) promoter operably linked to an sST2 nucleic acid. HSV amplicon vectors may also be useful in various methods of the invention. Typically, HSV amplicon vectors are approximately 15 kb in length, and possess a viral origin of replication and packaging sequences.

Alphavirus-based vectors, such as those made from semliki forest virus (SFV) and sindbis virus (SIN), might also be used in the invention. Use of alphaviruses is described in Lundstrom, K., Intervirology 43:247-257, 2000 and Perri et al., Journal of Virology 74:9802-9807, 2000. Alphavirus vectors typically are constructed in a format known as a replicon. A replicon may contain (1) alphavirus genetic elements required for RNA replication, and (2) a heterologous nucleic acid such as one encoding an sST2 nucleic acid. Within an alphavirus replicon, the heterologous nucleic acid may be operably linked to a tissue-specific promoter or enhancer.

Recombinant, replication-defective alphavirus vectors are advantageous because they are capable of high level heterologous (therapeutic) gene expression, and can infect a wide target cell range. Alphavirus replicons may be targeted to specific cell types (e.g., MSCs) by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell. A preferred alphavirus vector or replicon is non-cytopathic.

In many of the viral vectors compatible with methods of the invention, more than one promoter can be included in the vector to allow more than one heterologous gene to be expressed by the vector. Further, the vector can comprise a sequence, which encodes a signal peptide, or other moiety, which facilitates the expression of an sST2 gene product from the target cell.

To combine advantageous properties of two viral vector systems, hybrid viral vectors may be used to deliver an sST2 nucleic acid to the MSCs. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18: 176-186, 2000. Retroviral genomes contained within an adenovirus may integrate within the target cell genome and effect stable sST2 gene expression.

Other nucleotide sequence elements, which facilitate expression of the sST2 gene and cloning of the vector, are further contemplated. For example, the presence of enhancers upstream of the promoter or terminators downstream of the coding region, for example, can facilitate expression.

In addition to viral vector-based methods, non-viral methods may also be used to introduce an sST2 gene into a target cell. A review of non-viral methods of gene delivery is provided in Nishikawa and Huang, Human Gene Ther. 12:861-870, 2001. A preferred non-viral gene delivery method according to the invention employs plasmid DNA to introduce an sST2 nucleic acid into a cell. Plasmid-based gene delivery methods are generally known in the art. Synthetic gene transfer molecules can be designed to form multimolecular aggregates with plasmid DNA. These aggregates can be designed to bind to the MSCs.

Cationic amphiphiles, including lipopolyamines and cationic lipids, may be used to provide receptor-independent sST2 nucleic acid transfer into MSCs. In addition, preformed cationic liposomes or cationic lipids may be mixed with plasmid DNA to generate cell-transfecting complexes. Methods involving cationic lipid formulations are reviewed in Feigner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the invention. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun. 13:141-164, 1994.

Vectors containing nucleic acids that encode the expression of sST2 can be introduced to the MSCs that are cultured ex vivo or in vitro by direct delivery into the culture medium. The delivery preparation can contain a pharmaceutically acceptable carrier, such as saline, as necessary. Other pharmaceutical carriers, formulations and dosages can also be used in accordance with the present invention.

The airway immune inflammatory and lung diseases to be treated according to the present invention are selected from acute lung injury, Chronic Obstructive Pulmonary Disease including chronic bronchitis, emphysema, bronchiectasis and bronchiolitis, acute respiratory distress syndrome, asthma, hypersensitivity pneumonitis and pulmonary fibrosis. Where possible, said diseases, injures or syndromes include both acute and chronic pathological state.

In a particular embodiment, the MSC disclosed herein are in the form of single-cell suspensions, microcarriers or spheroids. In a particular embodiment, the method used in the treatment of airway immune inflammatory and lung diseases with the MSC of the present invention comprises the administration of said stem cells by parenteral or pulmonary route administration.

Preferably, said parenteral administration is via intravenous, intrapleural or intraarterial routes. Exemplary parenteral administration forms include solutions or suspensions of the MSCs in sterile aqueous solutions, for example, aqueous propylene glycol or dextrose solutions. Such dosage forms can be suitably buffered, if desired.

Said pulmonary route for administration is indeed a topical administration through the airways by means of, for example, sprays, nebulizers, vaporisers, intranasal or tracheal instillations. In a preferred embodiment, the MSC of the present invention are obtained from adipose tissue. In a second aspect the present invention relates to a pharmaceutical composition comprising the mesenchymal stem cells as disclosed in any of the embodiments of the present invention.

The pharmaceutical composition will include a conventional pharmaceutical carrier or excipient and the mesenchymal cells according to the invention as an active ingredient. In addition, it may include other medicinal or pharmaceutical agents, carriers, adjuvants, etc.

Suitable pharmaceutical carriers include inert diluents or fillers, water and various organic solvents. The pharmaceutical compositions may, if desired, contain additional ingredients such as flavorings, binders, excipients and the like.

The present invention also relates to a method of treating an airway immune inflammatory and lung disease including, but not limited to, acute lung injury, Chronic Obstructive Pulmonary Disease including chronic bronchitis, emphysema, bronchiectasis and bronchiolitis, acute respiratory distress syndrome, asthma, hypersensitivity pneumonitis and pulmonary fibrosis, in a mammal (e.g., human) comprising administering to said mammal a therapeutically effective amount of the MSCs genetically modified according to the present invention or a pharmaceutical composition comprising them.

The phrase "therapeutically effective amount" means in the present invention an amount of the MSCs genetically modified according to the present invention or a pharmaceutical composition that (i) treats the particular disease, condition or disorder, or (ii) attenuates, ameliorates, or eliminates one or more symptoms of the particular disease, condition, or disorder. The following examples illustrate the present invention but they are not intended to limit the scope of the invention.

Experimental Part
Materials and Methods
Isolation and Characterization of hASCs

Discarded human adipose tissue from a healthy adult woman undergoing elective lipoaspiration was used as the source of hASC, under the Institutional Ethics Committee approval, as described elsewhere (Moreno et al. (2011) Tissue Eng. 17: 275-87). Briefly, the raw lipoaspirate (200 ml) was washed extensively with phosphate buffered saline (PBS) and incubated in PBS containing 0.075% type II collagenase (Invitrogen, Carlsbad, Calif.) at 37° C. for 1 h to digest the extracellular matrix. The protease activity was neutralized with Dulbecco's modified Eagle's medium (DMEM, Invitrogen) plus 10% fetal bovine serum (FBS). The resulting suspension was filtered through a 70 μm nylon filter, centrifuged, resuspended in α-MEM (Invitrogen) containing 15% FBS, 1% penicillin/streptomycin, 1% L-glutamine and 2.5 μg/ml amphotericin (all from Invitrogen), and seeded overnight in culture flasks (Corning Inc., Corning, N.Y.) at 37° C. in a 5% $CO_2$ atmosphere. Next day, the cell monolayer was washed once more with PBS to remove nonadherent cells and cellular debris and replaced with fresh medium. Finally, the hASCs were expanded for 4-5 days (passage 0), substituting the culture medium every 2 days, until 80% confluent, amplified through periodic passaging (split ratio 1:2).

Adipogenic differentiation was induced by seeding hASCs for 21 days in Iscove's modified Dulbecco's medium (IMDM) supplemented with 0.5 mM isobutyl methyl xantine, 1 ηM hydrocortisone and 0.1 mM indomethacin. The cells containing lipid droplets were visualized by Oil Red-O staining. Osteogenic differentiation was induced by culturing hASCs in IMDM containing 0.1 μM dexametasone, 10 mM β-glycerol phosphate and 0.2 mM ascorbic acid for 21 days. Calcified extracellular matrix deposits were visualized after Alizarin Red staining. All hASC differentiation reagents were from Sigma-Aldrich (St. Louis, Mo.).

Flow cytometry to assess the expression levels of different surface markers was performed on a FACScan cytometer using CellQuest software (BD Biosciences, San Jose, Calif.) as previously described (Moreno et al. 2011). Briefly, hASCs (passage 4) were harvested by trypsinization, washed with PBS containing 1% bovine serum albumin and 0.1% sodium azide (all from Sigma-Aldrich) and stained with fluorescein isothiocyanate (FITC)- or phycoerythrin (PE)-conjugated antibodies against CD44, CD29 (Immunostep, Salamanca, Spain), CD90 (eBioscience, San 5 Diego, Calif.), CD14, HLA-DR and CD34 (BD Biosciences). The corresponding fluorescent isotype-matched negative control antibodies defined background staining.

sST2 Cloning, Lentiviral Vector Production and hASC Transduction

The full-length murine sST2 cDNA was obtained through RT-PCR amplification of mRNA harvested from LPS-stimulated NIH 3T3 mouse embryonic fibroblasts (ATCC CRL-1658). Briefly, NIH 3T3 cells were seeded in DMEM supplemented with 10% FBS, 1% penicillin/streptomycin, 1% L-glutamine and maintained at 37° C./5% CO2. To induce ST2 expression, NIH-3T3 cells were treated with LPS (10 µg/ml; Sigma-Aldrich) for 48 h. The cells were harvested and total RNA was isolated using the RNeasy kit (Qiagen, Hiden, Germany). The purified RNA was further treated with DNAse I (Ambion, Foster City, Calif.). Reverse transcription was performed on 1 µg of total RNA using the Omniscript RT kit (Qiagen). The expected 1 kb sST2 product was obtained after PCR amplification for 35 cycles (40 s denaturing at 95° C.; 1 min. annealing at 55; 1 min. elongation at 72° C.) using high-fidelity Easy-A thermostable DNA Polymerase (Stratagene, La Jolla, Calif.) and primers ST2 Forward: 5'-ATGATTGACAGACAGAGAAT-3' (SEQ ID NO: 5) and ST2 Reverse: 5'-AGCAATGTGTGAGGGACACT-3' (SEQ ID NO: 6). The PCR product was subcloned into the pGEM-T easy vector (Promega, Madison, Wis.) and verified by sequencing with primers seqST2 F: 5'-CACAGGTCCTACT-TGTTCATT-3' (SEQ ID NO: 7) and seqST2 R: 5'-GTTGGT-TCCATTCTCCGCGT-3'(SEQ ID NO: 8). Next, we constructed a bicistronic lentiviral vector encoding sST2 and EGFP cDNA sequences, separated by the porcine teschovirus-1 2A sequence (Doherty et al. (1999) J. Gen. Virol. 80:1929-41). Additionally, the FLAG sequence tag was introduced at the C-terminus of sST2 to differentiate recombinant from endogenous protein expression.

Therefore, the sST2 PCR product was further amplified with primers Adv-ST2F:

(SEQ ID NO: 9)
5'-TCGGCGCACGCTGGAAGACGCGGAGGCTCTCTTCAGTAAATACTGC

GATGATTGACAGACAGAGAATGGGACTT-3';

note that the underlined part belongs to DNA coding for the Adenovirus fiber protein and the rest belongs to ST2 from mouse) and 2A-FLAG-ST2 R:

(SEQ ID NO: 10)
5'-GCTTTAACAGAGAGAAGTTCGTGGCTCCGGACCCTCTAGACTTATCG

TCGTCATCCTTGTAATCATACGAGTCAGCAATGTGTGAGGGACACTCC

TTACT-3', note that the underlined part next to 5' belongs to porcine teschovirus-1 2A sequence, the central part belongs to a "FLAG-tag" peptide sequence (synthetic) and the underlined part next to 3' belongs to ST2 from mouse), including the FLAG sequence, and inserted into the adenoviral vector pVK50-CAUFiber2AEGFP (a kind gift from Ramon Alemany, ICO, Barcelona) through homologous recombination in yeast. The sST2-FLAG-2A-EGFP construct was re-amplified from the resulting plasmid, pVK50-CAU sST2FLAG2AEGFP, using primers pWPT-BamHI-ST2F:

(SEQ ID NO: 11)
5'-GTCGTGACGCGGATCCATGATTGACAGACAGAGAATGGGACTT-3', note that the underlined part belongs to the lentiviral vector sequence pWPTEGFP and the rest belongs to ST2 from mouse) and pWPT-SalI-EGFP R: 5' GGAATTCCCTCGAG-GTCGACTTACTTGTACGCTCGTCCAT-3'(SEQ ID NO: 12, note that the underlined part belongs to the lentiviral vector sequence pWPT-EGFP and the rest belongs to ST2 from mouse), which incorporated the unique restriction sites BamHI at the 5'-end, and Sal I at the 3'-end of the DNA sequence, respectively. Finally, the bicistronic construct was introduced into the BamHI/SalI-digested pWPT-EGFP lentiviral vector (kindly provided by Didier Trono, Geneve, Switzerland) to yield pWPT-sST2FLAG2AEGFP.

VSV-G-pseudotyped, high-titer lentiviral particles from vectors pWPTsST2FLAG2AEGFP and pWPT-EGFP were produced by transient triple-transfection on human embryonic kidney 293T cells as previously described (Moreno et al. (2009) Blood Cells Mol. Dis. 43: 214-20).

hASCs from passage 2-3 were transduced in suspension with the above lentiviral vector particles at several multiplicities of infection (MOI), ranging from 1 to 40. The culture medium was replaced after 16 h to remove lentiviral particles. At 48 h after transduction the EGFP expression was analyzed by both flow cytometry and fluorescence microscopy, and the mouse sST2 protein expression was assessed by a specific mouse T1/ST2 ELISA assay (mdbioproducts, Zurich, Switzerland) according to the manufacturer's instructions. The hASCs administered throughout the in vivo ALI model assays were transduced with the appropriate lentiviral vector particles at an optimized MOI of 20.

Western Analysis

Both pWPT-sST2-EGFP- and pWPT-EGFP-transduced hASCs were resuspended for 10 min on ice in a lysis buffer containing 50 mM Tris/HCl, pH 7.4, 5 150 mM NaCl, 1% Triton-X 100, 2 mM EGTA, 0.1% SDS, 0.5 mM deoxycolic acid, 1 mM PMSF and a protease inhibitor cocktail (Roche Diagnostics, IN). Cell debris was removed by centrifugation at 13000×g for 10 min at 4° C., and the protein concentration was measured using the bicinchoninic acid assay (BCA Protein Assay Kit, Pierce, Rockford, Ill.). Soluble extracts (50 µg from each sample) were resuspended in Laemmli's sample buffer and heated for 15 min at 98° C. Samples were resolved by SDS/10% polyacrylamide gel electrophoresis (PAGE) and transferred to Hybond-C Extra nitrocellulose membranes (Amersham Biosciencies). The following primary antibodies were used for detection: anti-FLAG Mouse monoclonal antibody M2 (Sigma-Aldrich; 1:1000 dilution) and anti-GFP Mouse monoclonal antibody (Santa Cruz Biotechnology, Santa Cruz, Calif.; 1:1000 dilution), both incubated o/n at 4° C. Anti-tubulin mouse monoclonal antibody (Sigma-Aldrich; 1:5000 dilution) incubated 1 h at room temperature was included for normalization. The signals were visualized by enhanced chemiluminescence (ECL) detection (Amersham Biosciences).

IL-33-sST2 Interaction

The mouse mastocytoma cell line P815 (a kind gift of Gaby Palmer, Genève, Switzerland) was cultured in DMEM High Glucose (Life Technologies) supplemented with 10% FBS and 1% penicillin/streptomycin, in a humidified incubator at 37° C. with a 5% $CO_2$ atmosphere.

P815 cells were plated in 96-well plates with 200 □l of complete culture medium, at a density of 20,000 cells per well, and stimulated with IL-33 (1 ng/ml). In some wells, supernatant from hASC-trasduced cells was added 15 min prior to stimulation. IL-6 levels in the cell supernatants were assessed by ELISA, according to the manufacturer's instructions (Diaclone, Besancon Cedex, France).

Murine Model of LPS-Induced ALI and Study Design

All procedures involving mice were reviewed and approved by the Ethical Committee of Animal Experimentation of the Vall d'Hebron Research Institute (Barcelona, Spain). Ten to twelve week-old male BALB/c mice (Harlan, Horst, The Netherlands) were anesthetized with 2% isoflurane and challenged with a single intranasal instillation of 8 mg/kg of LPS (*E. coli* 055:B5; Sigma-Aldrich) dissolved in 50 µl of PBS, or administered 50 µl of PBS alone. Six hours after the induction of injury, mice received hASCs, engineered hASCs expressing sST2 (hASC-sST2) ($1 \times 10^6$ cells in 200 µl of PBS in both cases), or 200 µl of PBS by tail vein injection. All mice were analysed at 48 h after LPS/PBS instillation (FIG. 1).

For each batch of hASC-sST2 employed, adequate sST2 protein expression levels were confirmed by ELISA, as indicated in the previous section.

Bioluminescence Imaging

For in vivo imaging, a bicistronic lentiviral vector (LV-T2A) encoding the firefly luciferase (fLuc) and the EGFP under the control of a cytomegalovirus promoter was used to generate reporter viral particles (Ibrahimi et al. (2009) Hum. Gene Ther. 20: 845-60). hASCs were efficiently transduced at a MOI of 20 and administered intravenously ($1 \times 10^6$ cells/mice) into LPS- or PBS-instilled mice at 6 h following endotoxin challenge, as indicated in the previous section. The mice were imaged at 30 min and 48 h after luciferase expressing-hASC administration in an IVIS$^R$ Spectrum Imaging System (Caliper Life Science, MA, USA). Anesthesia was performed in an induction chamber with 3% isoflurane in 100% oxygen at a flow rate of 1.25 L/min, and maintained in the IVIS system with a 2.5% of the above mixture at 0.5 L/min. The mice were intraperitoneally injected with D-luciferin (150 mg/kg) (Promega) dissolved in PBS.

In previous optimization assays, consecutive image scans were taken every 2 min up to about 30 min to define the optimal time range (5-15 min) for bioluminescent image capturing after D-luciferin injection. Each frame depicts the bioluminescence signal as a pseudo color image superimposed on the gray-scale photographic image. Bioluminescent signaling on the lungs was measured as integrated photons/second. Imaging data were analyzed using the Living Image 4.1 (Caliper Life Science). For ex vivo imaging, just prior to euthanasia (by intraperitoneal injection of 90 mg/kg pentobarbital) mice were injected intraperitoneally with D-luciferin (150 mg/kg). Immediately after necropsy, mouse lungs were placed individually into separate wells containing 300 □g/ml D-luciferin, and imaged. Two consecutive 1 min scans were acquired and the lung was dissected, placed in a plate and sliced into different lung lobes. These were imaged for 1 min in the IVIS.

Bronchoalveolar Lavage, Cell Count and Protein Measurement

Bronchoalveolar lavage (BAL) was performed in the treated mice at 48 h after intranasal instillation. The lungs were lavaged three times in situ with 0.7 ml of sterile saline (0.9% NaCl) at room temperature, and the recovered fluid was pooled. Cells were counted with a hemocytometer (total cells), and the BAL fluid (BALF) was centrifuged (1,500 g, 10 min). The supernatant was frozen (−80° C.) until further analysis. For differential cell counts, a 250 µl aliquot of the re-suspended cells (1 ml) was spun (1,400 g, 6 min) (Cytospin 3, Shandon, TechGen, Zellik, Belgium) onto microscope slides, air dried, and stained (Diff-Quick method). For each sample, 1,000 cells were analyzed for macrophage, neutrophil, and lymphocyte number assessment. Total protein was measured in the BALF by the BCA assay (Pierce).

BALF and Plasma Cytokine/Chemokine Assessment

Levels of murine TNF-α, IL-6 (both from Diaclone, Besancon Cedex, France), MIP-2 (IBL, Gunma, Japan) and IL-33 (R&D Systems, Abingdon, UK), were measured in undiluted BALF and in serum (from blood drawn by cardiac puncture and centrifuged for 30 min at 2000 g) by sandwich enzyme-linked immunosorbent assays (ELISA), according to the manufacturer's instructions.

Histophatology and Immunohistochemistry

The trachea from hASC-, hASC-sST2-, and PBS-treated ALI animals not undergoing BAL was cannulated at 48 h post-LPS induction, and the lungs were fixed by inflation to total lung capacity with 1 ml of 4% paraformaldehyde. Following overnight fixation, the lung tissue was embedded in paraffin, cut into 3 µm thick sections, and stained with hematoxylin and eosin. Images were taken with an Olympus BX41 microscope (Olympus Life Science Research GmbH, Munich, Germany) using a 40x objective. To determine morphology and inflammatory infiltrate, images were evaluated by a pathologist who was blinded to the identity of the slides. Histological evidence of tissue injury was measured according to the American Thoracic Society lung injury scoring system (Matute-Bello et al. (2011) Am. J. Respir. Cell Mol. Biol. 44: 725-38).

For immunohistochemistry, formalin-fixed tissues were dehydrated with an ethanol gradient, cut and embedded in paraffin. Sliced 5 □m sections were mounted on poly-Ll-ysine-coated glass slides and immunostained as previously described (Moreno et al (2011) Stem Cells Dev. In Press, DOI: 10.1089/scd.2010.0483). Briefly, sections were deparaffinized and re-hydrated. Immunogenic retrieval was performed incubating the slides in 10 mM citrate buffer pH 6.0 for 20 min in a microwave oven. Following several PBS-T (PBS plus 0.1% Triton X-100) washes, tissue sections were blocked by 2 h incubation in 5% goat serum diluted in PBS-T at room temperature. Further, PBST washed sections were incubated overnight at 4° C. in a humid chamber with a polyclonal rabbit anti-Ki67 antibody (Invitrogen) diluted 1:100 in PBS-T. Next day, sections were incubated with a biotin-conjugated goat anti-rabbit IgG antibody (Invitrogen) in PBS for 1 h at room temperature, and the endogenous peroxidase was blocked with 3% H2O2 for 10 min in the dark. Finally, the sections were incubated with a biotinylated horse-radish peroxidase-avidin complex (ImmunoPureR ABC Peroxidase Staining Kit; Pierce). Finally, sections were stained with the peroxidase substrate diaminobenzidine tetrahydrochloride (DAB, Pierce) and counterstained with hematoxylin. Specificity control slides were analogously stained using nonimmune rabbit IgG (1:100 dilution) (Abcam, Cambridge, UK) as primary antibody.

RNA Isolation and Analysis

Mouse lung tissue was immediately frozen in liquid nitrogen after euthanasia. Total lung RNA was isolated using the RNeasy Mini kit (Qiagen). After isolation, RNA samples were DNase-treated for 60 min at room temperature to remove contaminating DNA. Gene expression analysis from hASC-treated and untreated mouse lung RNA was performed through reverse transcription followed by real-time quantitative TaqMan polymerase chain reaction (TaqMan RT-qPCR; PE Applied Biosystems, Foster City, Calif.). Specific TaqMan gene expression assays for human Ki67, IDO, TGF-β, COX-2, and GUSB as the housekeeping gene, and for mouse IL-33, TLR4, IL-10, IFN-□ and Cebpa as the housekeeping counterpart, were run in triplicate and analyzed in a spectrofluorimetric thermal cycler (ABI PRISM 7300 Sequence Detector (PE Applied Biosystems). Data quantification was carried out through the comparative Ct method.

Lung Mechanics Measurement

Two days after the induction of LPS-mediated airway injury, lung mechanics was analyzed using a FlexiVent ventilator (FlexiVent, SCIREQ, Montreal, PQ, Canada). Briefly, mice were deeply anaesthetized by intraperitoneal administration of ketamine (75 mg/kg) plus xylazine (1 mg/kg), tracheostomized with an 18-gauge cannula, and quasi-sinusoidally ventilated with a tidal volume of 7 ml/kg at a frequency of 150 breaths/min and a positive end expiratory pressure of 2 cm H2O. To avoid any spontaneous breathing, the animals were administered intraperitoneally a dose of 6 mg/kg of rocuronium. Next, forced oscillation perturbation was applied. In this perturbation, a broad 8 sec band frequency (0.5 to 19.75 Hz) produced by the ventilator allows recording mechanical parameters such as specific airway resistance (Rn), inertia of the air (I), tissue damping (resistance) (G), and tissue elasticity (H). At the end of the measurements, mice were sacrificed by intraperitoneal injection of 90 mg/kg of pentobarbital. Subsequently, bronchoalveolar lavage, serum and lung tissue were collected from each mouse for further analyses.

Statistical Analysis

Unless otherwise indicated, data are represented as mean values±SEM, or as individual points in a vertical dot plot, with a line to indicate the mean value. Differences between groups were assessed using a one-way ANOVA, adjusted for multiple comparisons (Bonferroni's test), where appropriate. (GraphPad Prism 5.00; GraphPad Software Inc., San Diego, Calif.). In all instances, a p value <0.05 was considered statistically significant.

Results

Generation and Characterization of hASCs Overexpressing Murine sST2

Figure 2A:
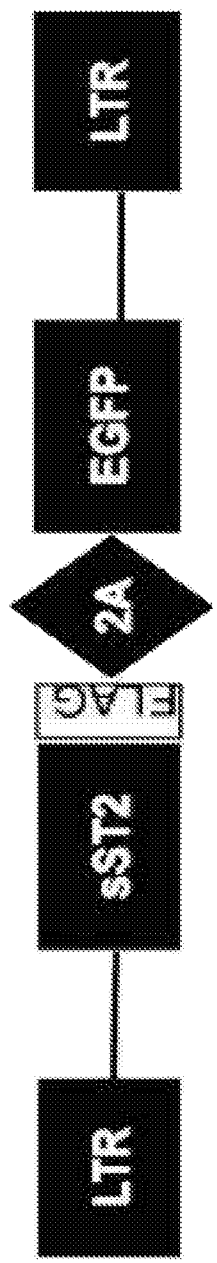
FIG. 2A-FIG. 2B. Generation and functional characterization of genetically engineered hASCs over-expressing sST2.
Figure 2B:
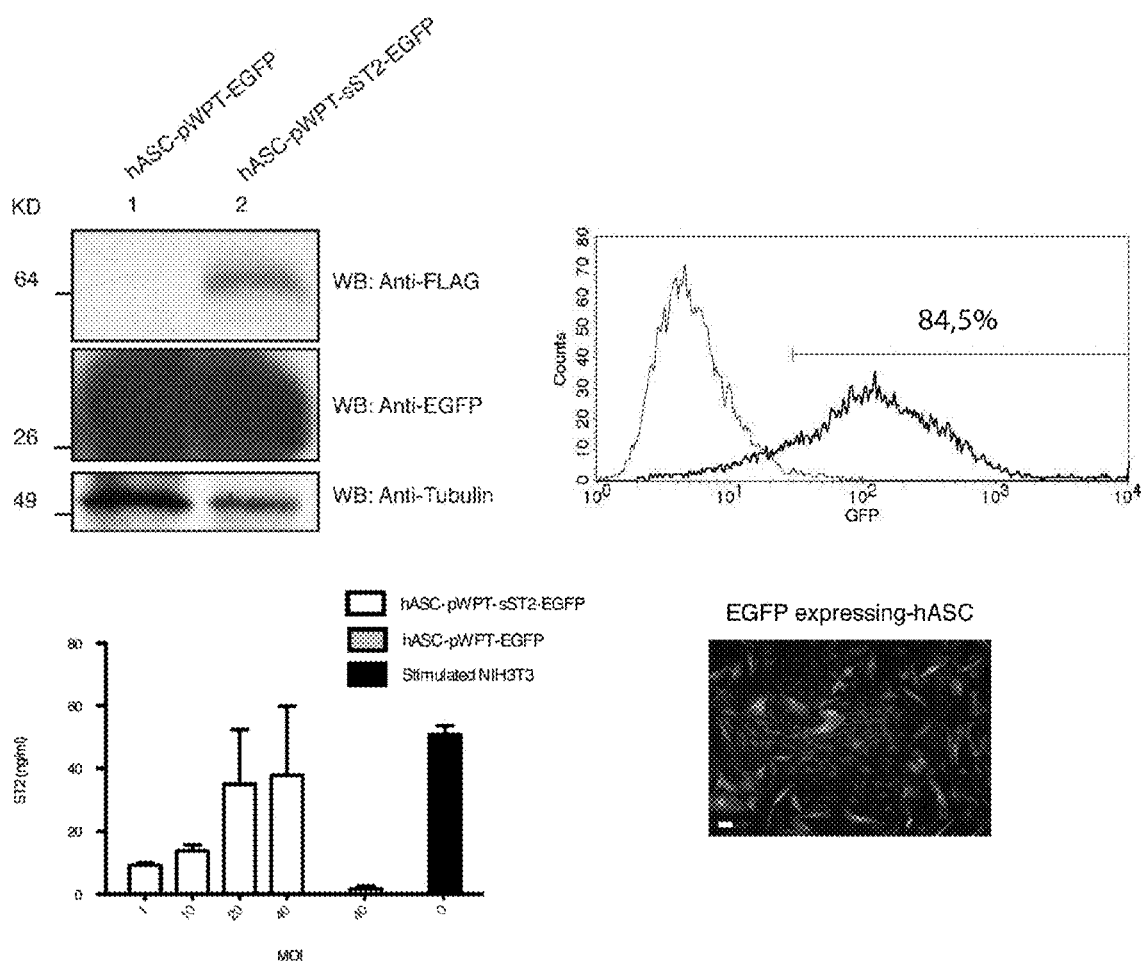
Figure 3:
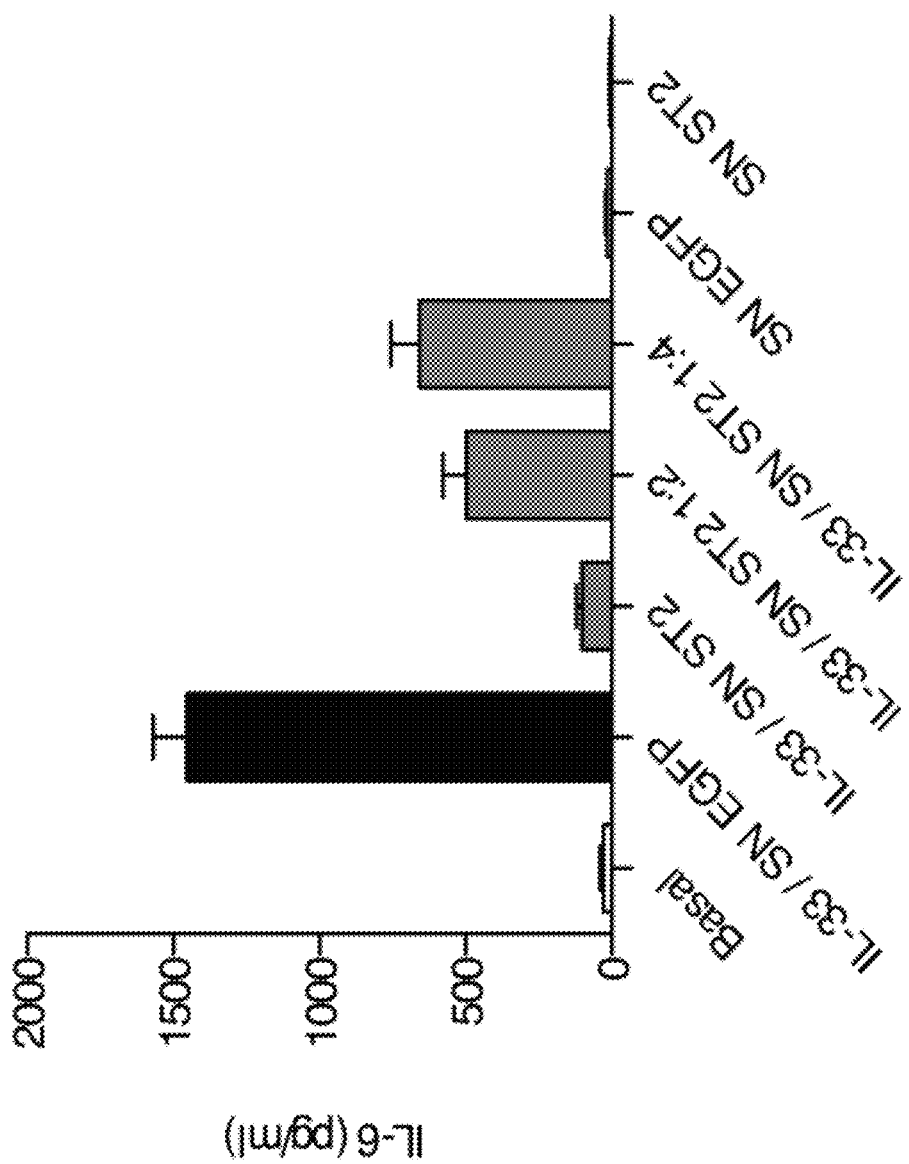
FIG. 3. sST2-FLAG secreted from pWPT-sST2-EGFP-transduced hASCs interferes with IL33-T1/ST2-mediated IL-6 production by P815 mastocytoma cells. Prior to stimulation, IL-33 (1 ng/ml) was co-incubated for 15 min at 37° C. with culture supernatants from pWPT-EGFP-transduced hASCs (SN-EGFP), or from pWPT-sST2-EGFP-transduced hASCs (SN-sST2) at different dilutions (undiluted, 1:2, and 1:4). The resulting mixtures were added to P815 cells for 48 h, and the induced IL-6 levels were assessed in the corresponding culture supernatants by ELISA. Control samples included untreated P815 supernatants (basal), and non-induced (no IL-33), SN-EGFP- or SN-sST2-treated supernatants. Results shown are represented as means±SD including triplicate measurements from 3 independent experiments.
Figure 11A:
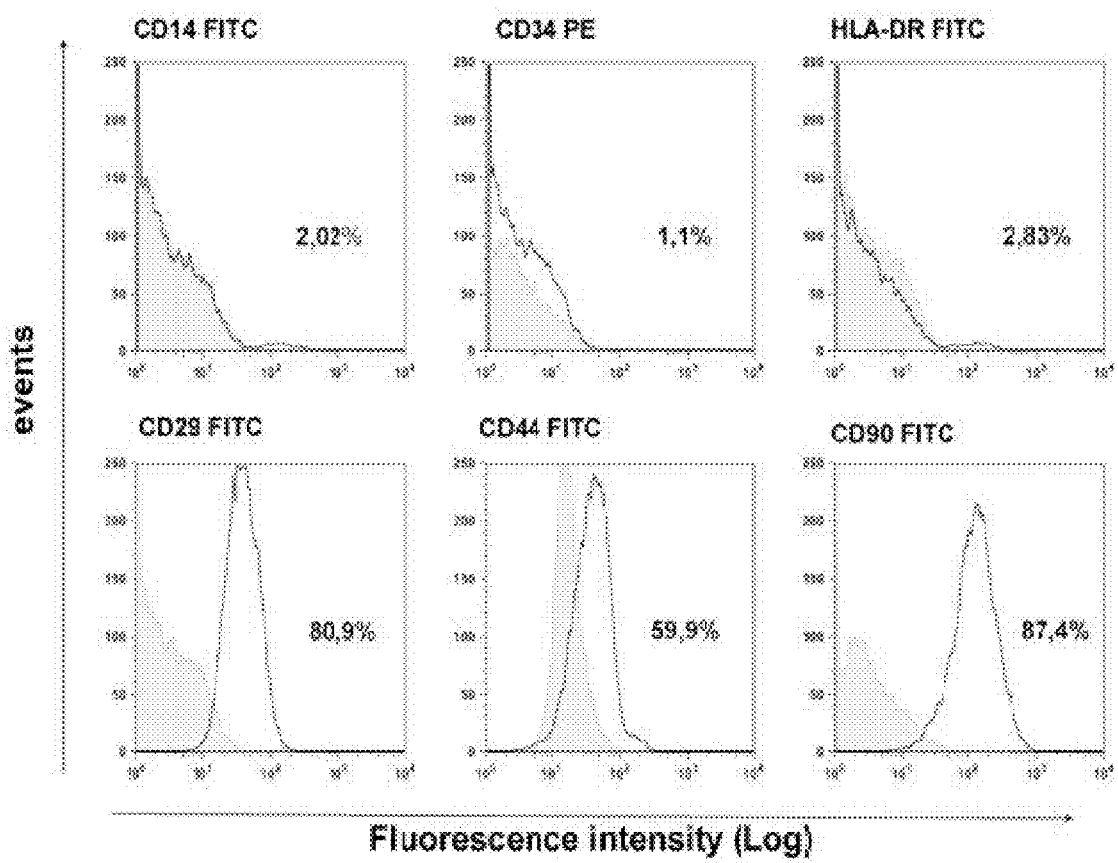
FIG. 11. Phenotypic and multipotent traits of lipoaspirate-derived hASCs. (A) Flow cytometry analysis of CD14, CD34, HLA-DR, CD29, CD44, and CD90 cell surface markers on the hASCs employed in this study. White histograms represent the distribution of the hASC population stained with each of the surface markers respect to their corresponding isotype controls (grey histograms). The values shown quantify the percentage of positive cells for a given marker. (B) The hASC population (passage 4) was induced during 21 days toward adipocytic differentiation, visualized by Oil Red staining (left panel), or toward osteocytic differentiation, visualized by Alizarin Red staining (middle panel). Confluent, non-induced hASCs at the end of the differentiation period showed the typical fibroblast-like appearance of undifferentiated cells (right panel). Bars indicate ×20 magnification.
Figure 11B:
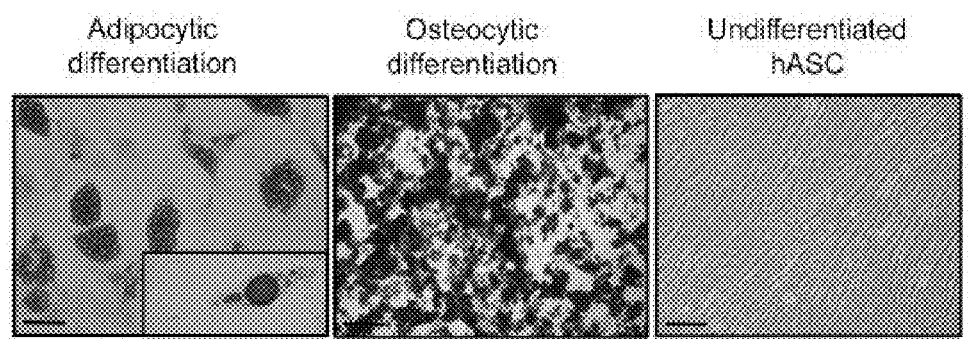

Growing evidence supports an important role of IL-33 in innate airway inflammation. Thus, we aimed exploring whether genetic engineering of hASCs as vectors and factories of the IL33 decoy receptor sST2 could endow them with additional or synergistic therapeutic benefit upon transplantation in a mouse ALI model. A thorough phenotypic and functional characterization was first performed on the adherent fibroblast-like hASCs isolated from lipoaspirates (Moreno et al. (2011) Tissue Eng. 17: 275-87, and FIG. 11). Next, we designed a bicistronic lentiviral vector incorporating a picornaviral 2A sequence flanking in a 5' to 3' orientation the C-terminus FLAG-tagged murine sST2 cDNA and the reporter EGFP cDNA (FIG. 2A). Transduction of hASCs with the above lentiviral vector confirmed the co-translational cleavage of the polyprotein product into the murine sST2-FLAG peptide and the reporter EGFP by Western blot analysis. The EGFP reporter also permitted visualizing and estimating the transduction efficiency of hASCs by both flow cytometry and fluorescence microscopy (FIG. 2B). Moreover, increasing the MOI correlated with an augmented production and secretion of recombinant murine sST2 by hASCs. Thus, at a MOI of 20 we reached an average 80±5% transduction efficiency, and a level of secreted sST2 (50±15 ng/ml) comparable to that induced by LPS treatment of NIH 3T3 fibroblasts (FIG. 2B). This optimized MOI of 20 was selected for the transduction of the hASCs employed in all the in vivo administration assays. Moreover, we evaluated the functionality of recombinant murine sST2-FLAG secreted by the transduced hASCs. The sST2-FLAG antagonist was able to significantly interfere, in a dose-dependent manner, with IL-33-T1/ST2 signaling in P815 mouse mastocytoma cells, reducing pro-inflammatory IL-6 induction (Moulin et al. (2007) Cytokine 40:216-225) (FIG. 3). As previously reported (Moreno et al. (2011) Tissue Eng Part C: Methods 17:275-287), lentiviral vector-mediated hASC transduction was able to modify neither its phenotype nor its functional properties (data not shown).

Figure 4A:
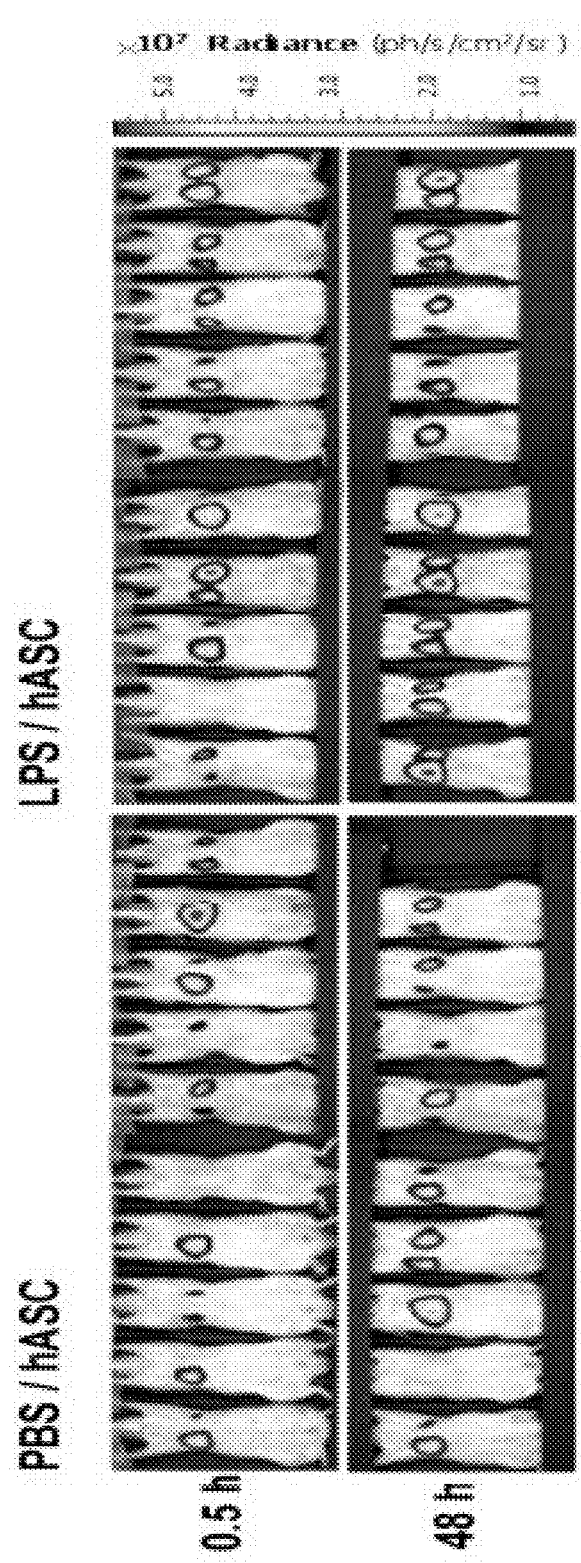
FIG. 4. Non-invasive in vivo imaging of hASC biodistribution into unchallenged and endotoxin-challenged ALI mice. Bioluminescent signals as a consequence of fLuc activity generated by LV-T2A-transduced hASCs intravenously injected into mice ($1\times10^6$ cells/mouse). (A) Representative graphic images of bioluminescence were recorded at 0.5 h and 48 h after hASC administration in both control PBS-instilled mice (left panels), and LPS-instilled mice (right panels). The coloured scale (represented in photons/s/cm$^2$/sr) next to the images indicates the signal intensity, where red and blue represent the highest and lowest signal intensity, respectively. (B) Bar diagram of in vivo fLuc activity quantification. Photon flux (ph/s) values were extracted from the recorded images (above) and plotted versus the elapsed time post-hASC inoculation, after background subtraction. *$p<0.05$, LPS versus PBS (n=10 mice per group). (C) Graphic images showing the ex vivo bioluminescent signal detected in lungs from 4 representative animals per group at 48 h post intravenous hASC administration.
Figure 4B:
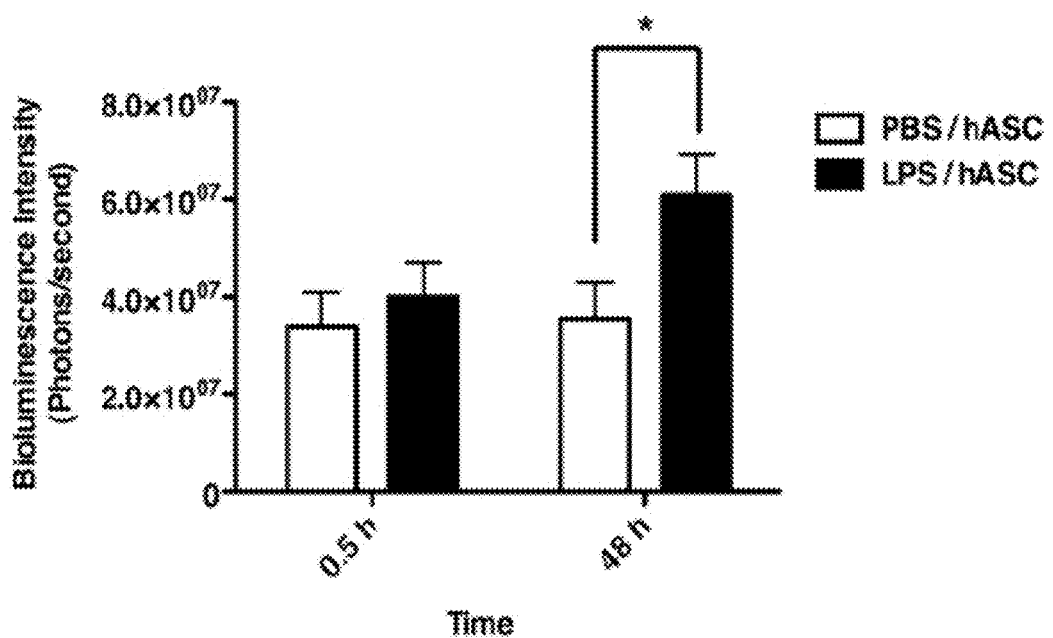
Figure 4C:
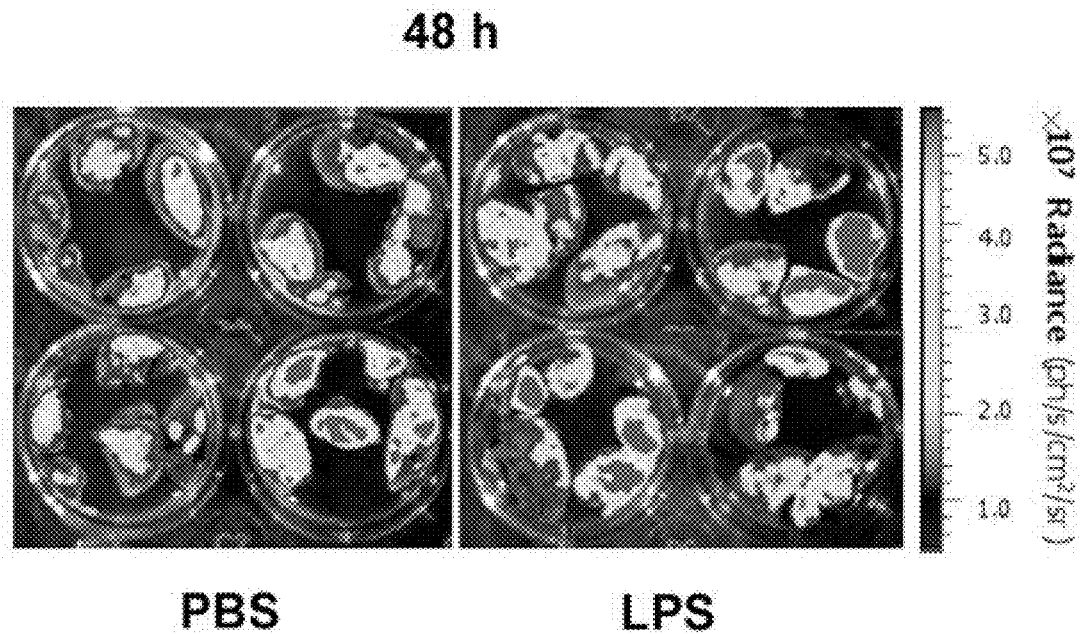
Figure 5A:
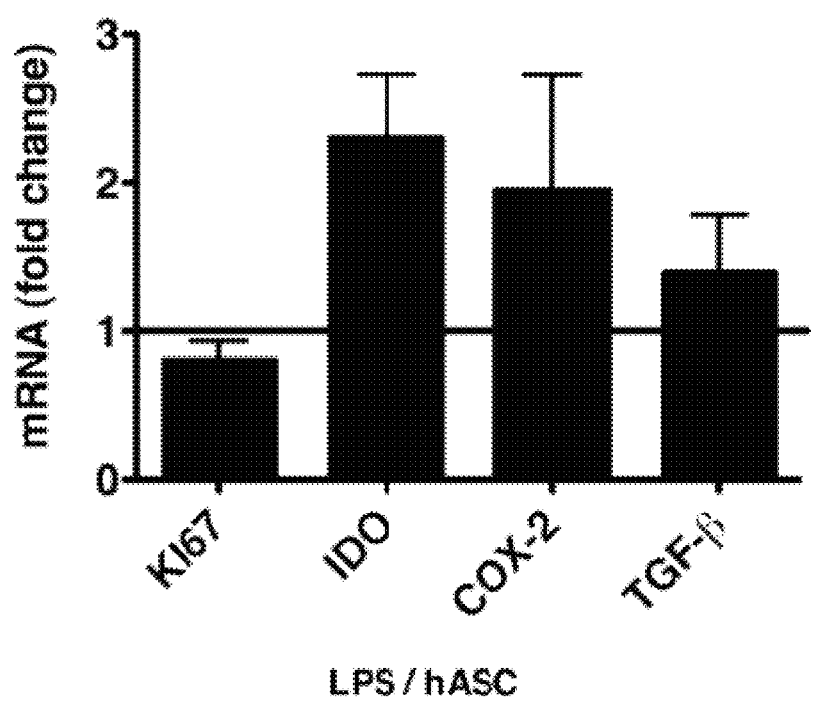
FIG. 5. Activation status of hASCs after intrapulmonary homing in the mouse ALI model. (A) The relative mRNA expression of the proliferation marker gene human Ki67, and the hASC activation genes IDO, COX-2, and TGF-β in hASC-treated murine lung tissue was determined by TaqMan RT-qPCR. Data are represented as fold induction of the indicated gene from LPS-induced and hASC-treated mice (LPS/hASC) respect to the same gene from PBS-instilled and hASC-treated mice (PBS/hASC) (n=3). (B) Representative immunohistochemistry images of human Ki67-stained lung tissue from hASC-treated mice at 48 h after LPS-induction (LPS/hASC) or PBS-instillation (PBS/hASC) (upper panels). Corresponding control images of Ki67-stained lung tissue from LPS- and PBS-instilled and untreated mice (lower panels). Arrows indicate positive staining. Magnification, ×200.
Figure 5B:
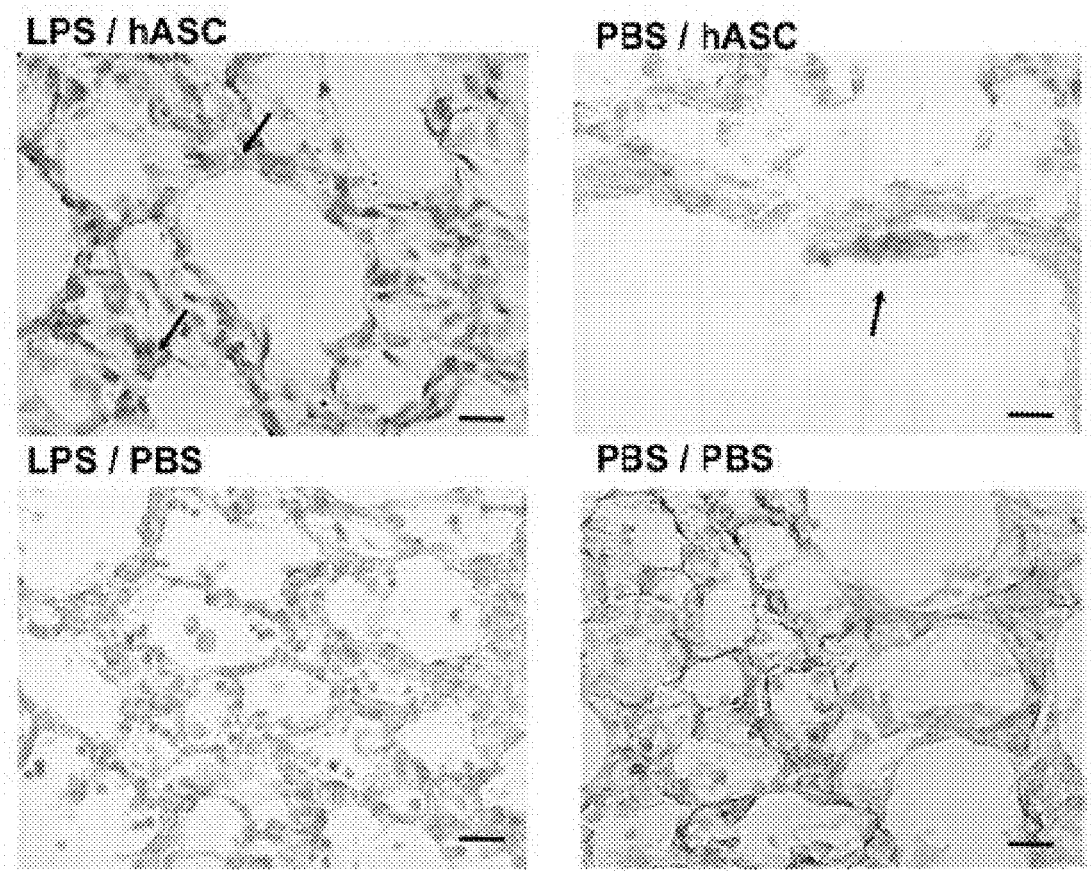

Behaviour of Transplanted hASCs in the Mouse ALI Model: Homing and Activation Status We performed preliminary studies evaluating the in vivo organ biodistribution of hASCs at two different times following their intravenous administration in a mouse ALI model generated by intranasal instillation of the endotoxin LPS according to the specified experimental design (FIG. 1). Lentiviral vector-mediated transduction of hASCs with the bicistronic fLuc-2A-EGFP configuration facilitated the sensitive tracking of the infused hASCs by bioluminescence imaging. The exclusive presence of the bioluminescent signal into the lungs of the transplanted animals, irrespective of PBS or LPS instillation, confirmed the tropism of intravenously infused hASCs to the lungs (FIG. 4A). Conversely, at 48 h after transplantation, a significantly increased presence of hASCs was evident in the LPS-instilled lungs when compared with the PBS-instilled control lungs (FIGS. 4B and 4C). This increase was not due to hASC proliferation, as the transcriptional levels of the human Ki67 proliferation marker were equivalent between LPS- and PBS-instilled mice (FIG. 5A). On the other hand, hASC activation in the LPS-induced pro-inflammatory milieu of the lung was evident by up-regulation of key anti-inflammatory transcripts such as IDO, COX-2 and TGF-β (FIG. 5A). Furthermore, immunostaining of the human Ki67 protein from the infused hASCs revealed significant differences in their cellular localization between the lung tissue from PBS-instilled mice (scarce presence and focal distribution) and that from LPS-induced mice (more frequent presence and homogeneous distribution) (FIG. 5B), as a consequence of vascular leakage and lung injury.

Thus, pro-inflammatory lung injury seems to promote hASC homing and activation, although not proliferation, in the mouse ALI model.

Figure 6:
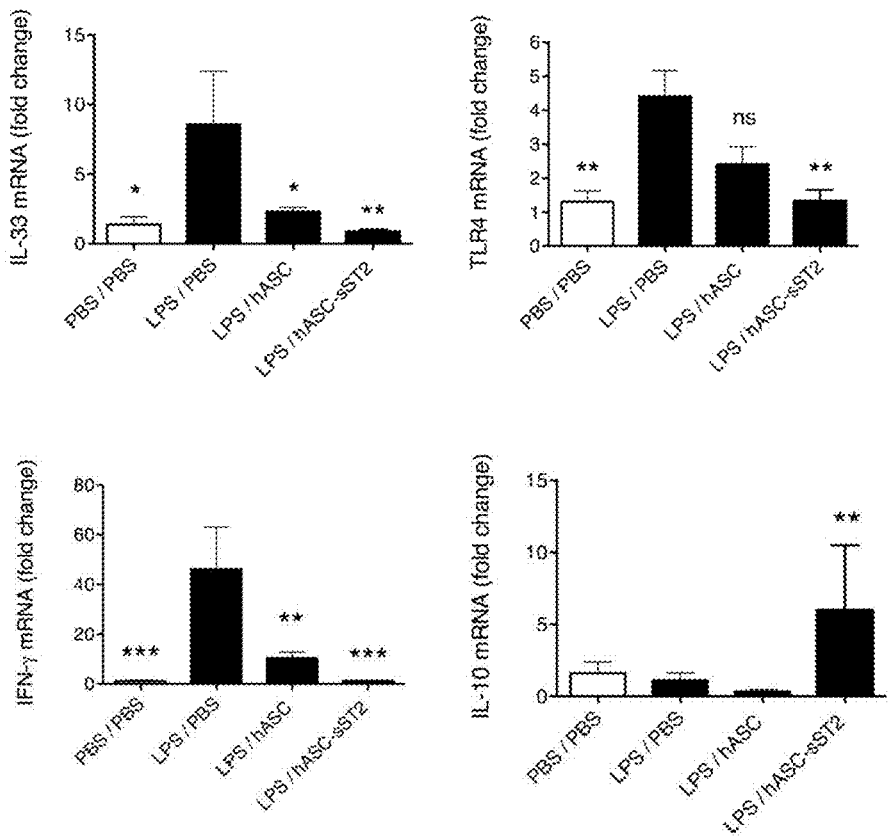
FIG. 6. Involvement of pro-inflammatory IL-33/ST2/TLR4 signalling in the endotoxin-induced ALI model. (A) The relative mRNA expression of murine IL-33 (n=3-5 per group), TLR-4 (n=6-8 per group), IFN-□ (n=4-5 per group), and IL-10 (n=4-5 per group) were measured in lung tissue by TaqMan RT-qPCR at 48 h after LPS or PBS instillation. Data are represented as fold induction of the indicated gene from LPS-challenged and untreated (LPS/PBS) or hASC-treated mice (LPS/hASC and LPS/hASC-sST2) (black columns), relative to the same gene from PBS-instilled, untreated mice (PBS/PBS) (white columns). (B) Serum IL-33 levels from control, PBS-instilled (PBS/PBS) (white column), and LPS-challenged, untreated mice (LPS/PBS), LPS-challenged plus hASC-treated mice (LPS/hASC) and LPS-challenged plus hASC-sST2-treated mice (LPS/hASC-sST2) (black columns) (n=8-9 per group), were determined by ELISA as indicated in *Materials and Methods*. (*p<0.05, p<0.01; p<0.001 compared to the LPS/PBS group; ns, non significant).
Figure 6:
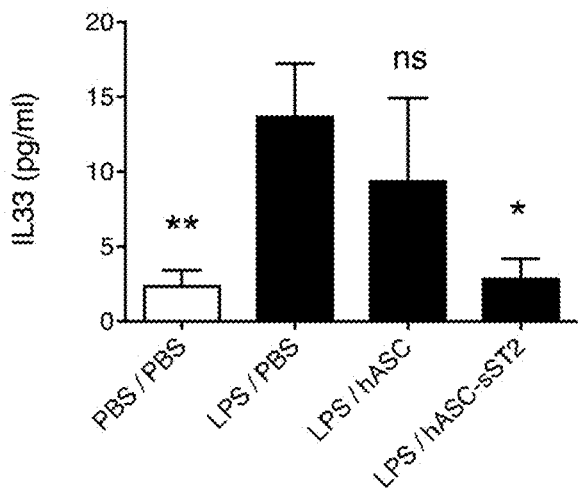

Superior Therapeutic Effect of hASCs Overexpressing sST2 on Acute LPS-Induced Pulmonary Inflammation It has been suggested that endotoxin-induced ALI could be regulated by the ST2-IL-33 and ST2-TLR4 axes (Sweet et al. (2001) J. Immunol. 166: 6633-9; Yin et al. (2011) Int. Immunopharmacol. 11: 2112-2117; Lefrancais et al. (2012) Proc. Natl. Acad. Sci. USA 109:1673-1678; Zhao et al. (2012) Nat. Immunol. 13:651-658). Thus, we wished to assess whether unmodified or sST2-overexpressing hASCs would be able to modulate the expression of pro-inflammatory mediators related with sST2: IL-33 and TLR-4, as well as other relevant inflammatory cytokines, such as IFN-γ and IL-10 in the LPS-injured lungs. Thus, while hASC treatment was able to reduce the expression of the above pro-inflammatory mediators (IL-33, TLR-4, IFN-γ) at different levels in the LPS-instilled mice, hASC-sST2 treatment was able not only to prevent its transcriptional induction, but also to induce the anti-inflammatory cytokine IL-10, as assessed by RT-qPCR from mRNA isolated from lung homogenates (FIG. 6A).

Moreover, although undetectable in the BALF, an increased production of pro-inflammatory IL-33 was observed in the sera of LPS-instilled mice at 48 h after instillation. To note, hASC-sST2-treated mice prevented the overproduction of circulating IL-33 mediated by LPS (FIG. 6B).

Figure 7:
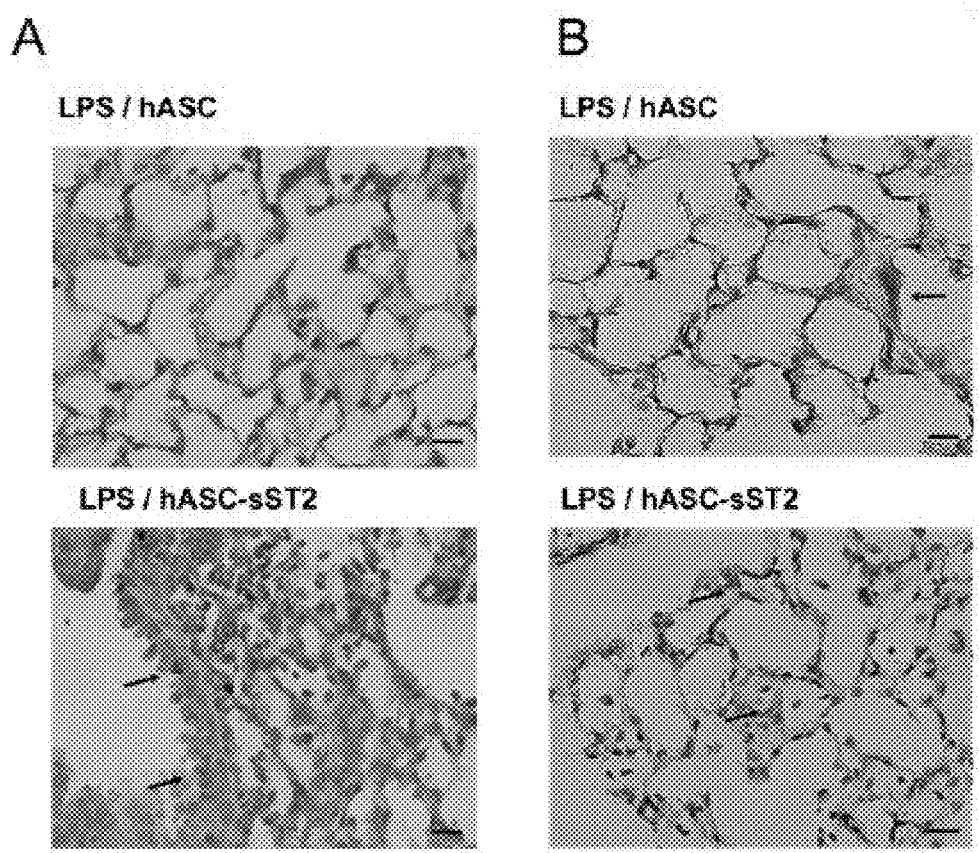
FIG. 7. Immunohistochemical localization of pWPT-sST2-EGFP-transduced hASCs over-expressing both murine sST2-FLAG and EGFP in the endotoxin injured lungs. Representative lung section images of LPS-induced, hASC-treated mice (LPS/hASC) (upper panels), and LPS-induced, hASC-sST2-treated mice (LPS/hASC-sST2) (lower panels) at 48 h after LPS instillation. Arrows indicate the brown label detection of sST2-FLAG-overexpressing hASCs (A), and of EGFP over-expressing hASCs (B). Magnification, ×400.

Taking into account the above evidences, we sought elucidating whether combining the anti-inflammatory and immune-modulatory actions of sST2 and hASCs yielded a superior therapeutic effect than administering hASCs alone in the murine model of LPS-induced ALI (FIG. 1).

hASCs overexpressing the sST2-FLAG transgene were immunolocalized into the LPS injured lungs from all hASC-sST2-transplanted mice, but not into control LPS-injured lungs from hASC-transplanted mice, which evidenced the local delivery of this anti-inflammatory decoy into the inflamed lung parenchyma (FIG. 7). Moreover, the unequivocal presence of hASCs in the transplanted lungs was corroborated by reporter EGFP expression (FIG. 7). Macroscopically, LPS-instilled and PBS-treated mice evidenced overt symptoms of endotoxemia at 48 h after challenge, characterized by hunched appearance, raised hair, sweating, reduced locomotor and exploratory behaviour and decreased responses to external stimuli. In contrast, mice instilled with LPS and treated with hASCs or hASCsST2 showed a lesser degree of sickness when evaluated by the above-mentioned symptoms. Moreover, upon gross lung examination of the LPS-instilled mice, those further PBS-treated evidenced petechial haemorrhages and necrotic lung lobes, whereas considerably fewer morphological alterations or lesions were seen in the lungs of hASC- or hASC-sST2-treated mice.

Figure 8A:
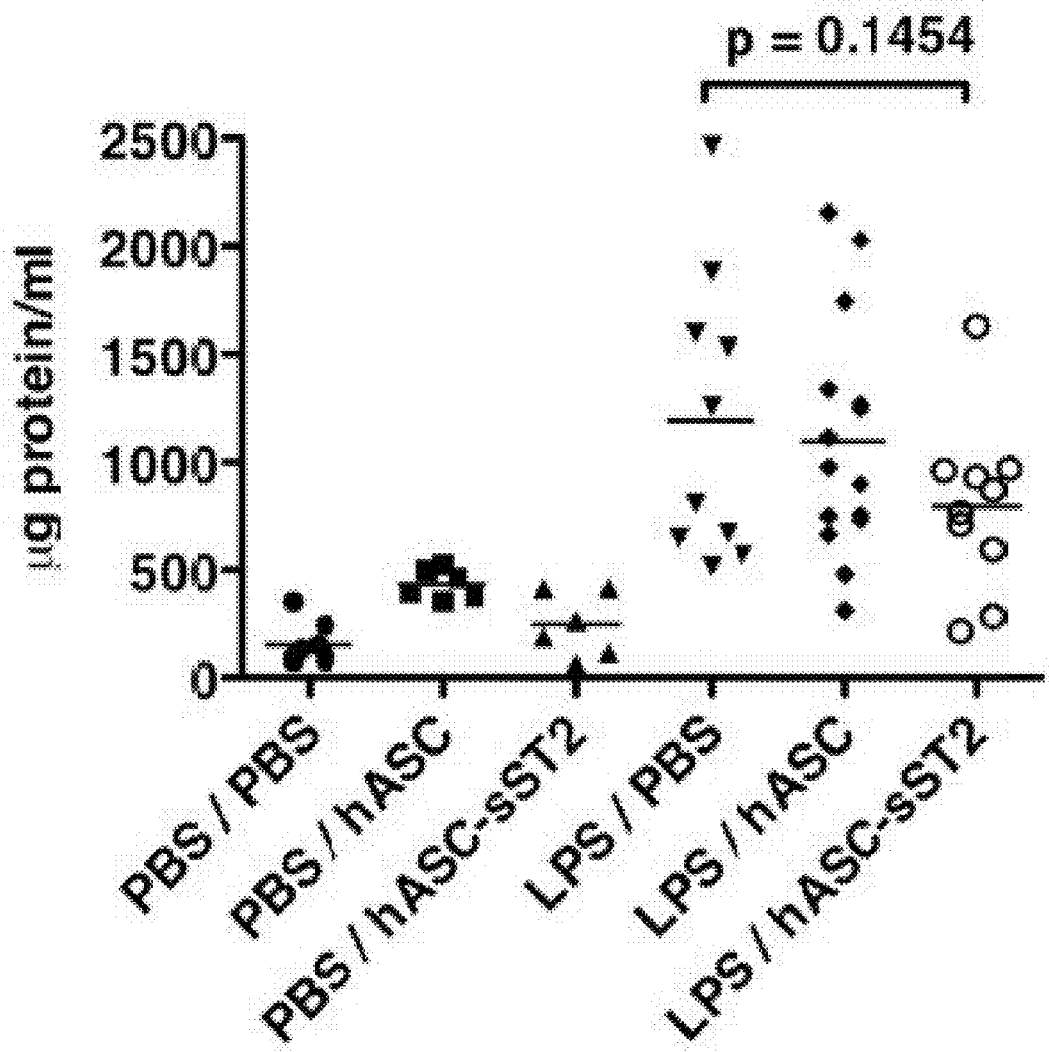
FIG. 8. BALF protein level plus total cell and neutrophil counts after LPS-induced lung inflammation in mice. Vascular leakage measured by total protein accumulation in the BALF (A), and numbers of inflammatory cells (B), and neutrophils (C) in the lung airspace were determined at 48 h after LPS/PBS instillation. PBS/PBS, PBS-instilled, untreated mice; PBS/hASC, PBS-instilled, hASC-treated mice; LPS/PBS, LPS-induced, untreated mice; LPS/hASC, LPS induced, hASC-treated mice; LPS/hASC-sST2, LPS-induced, hASC-sST2-treated mice (PBS-instilled groups, n=6-8; LPS-induced groups, n=8-16) (*p<0.05; p<0.01; *p<0.001 versus the LPS/PBS group).
Figure 8B:
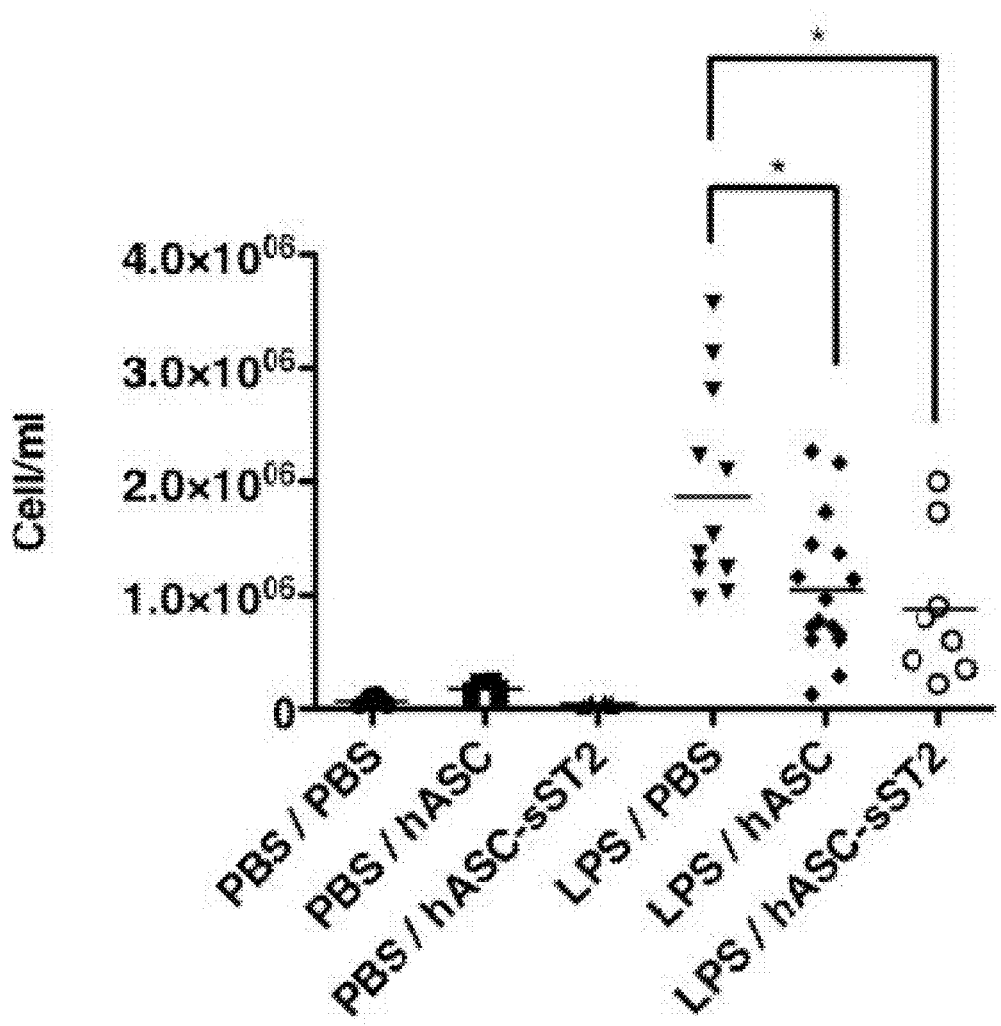
Figure 8C:
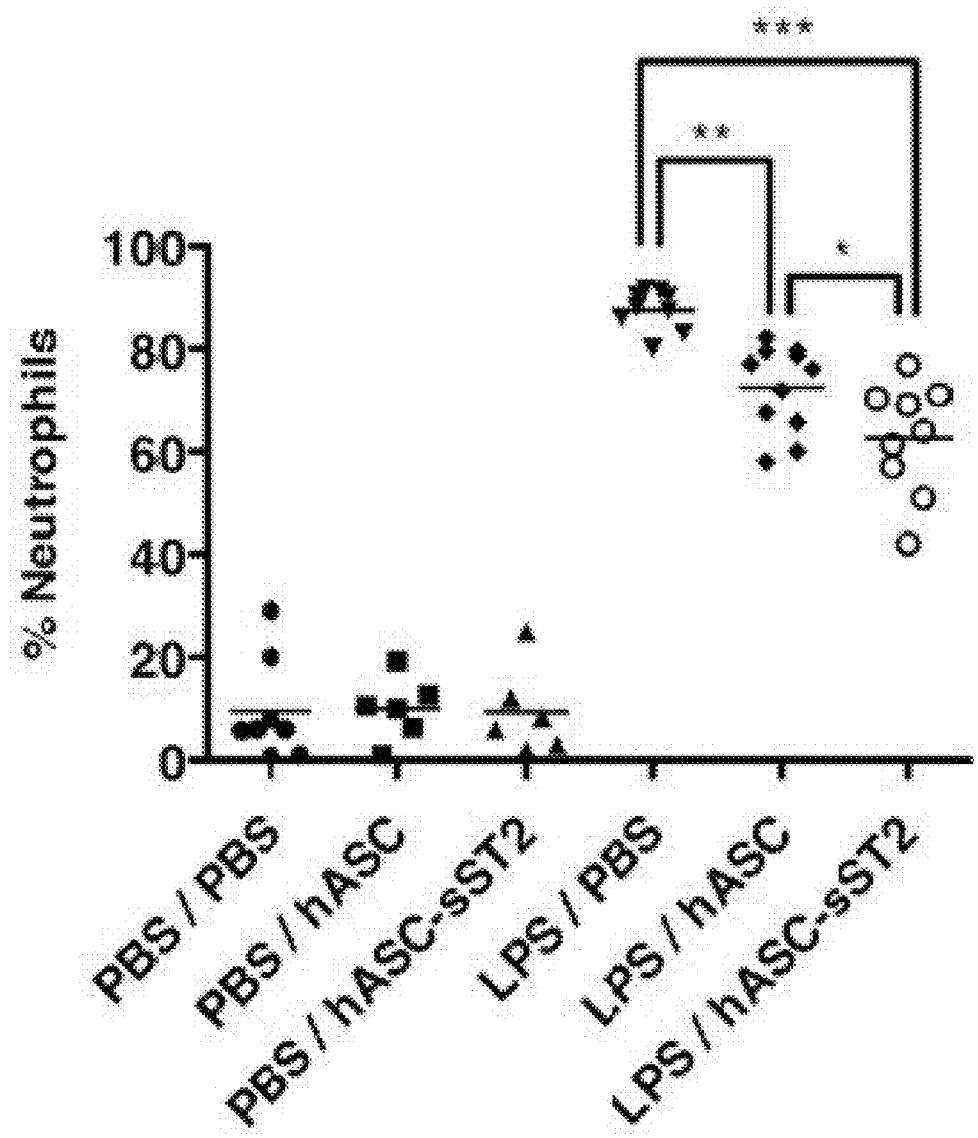

Microscopically, when compared with PBS-instilled control mice, LPS-instilled mice experienced marked pro-inflammatory alterations in the lungs, such as pulmonary vascular leakage, oedema and immune cell shedding into the epithelial lining fluid at 48 h after endotoxin challenge. Notably, total protein content, immune cell count and, particularly, neutrophil count in the BALF of hASC-treated mice were clearly decreased respect to those observed in untreated mice. These pro-inflammatory parameters were further attenuated by lung sST2 overexpression in hASC-sST2-treated mice (FIG. 8).

Figure 9A:
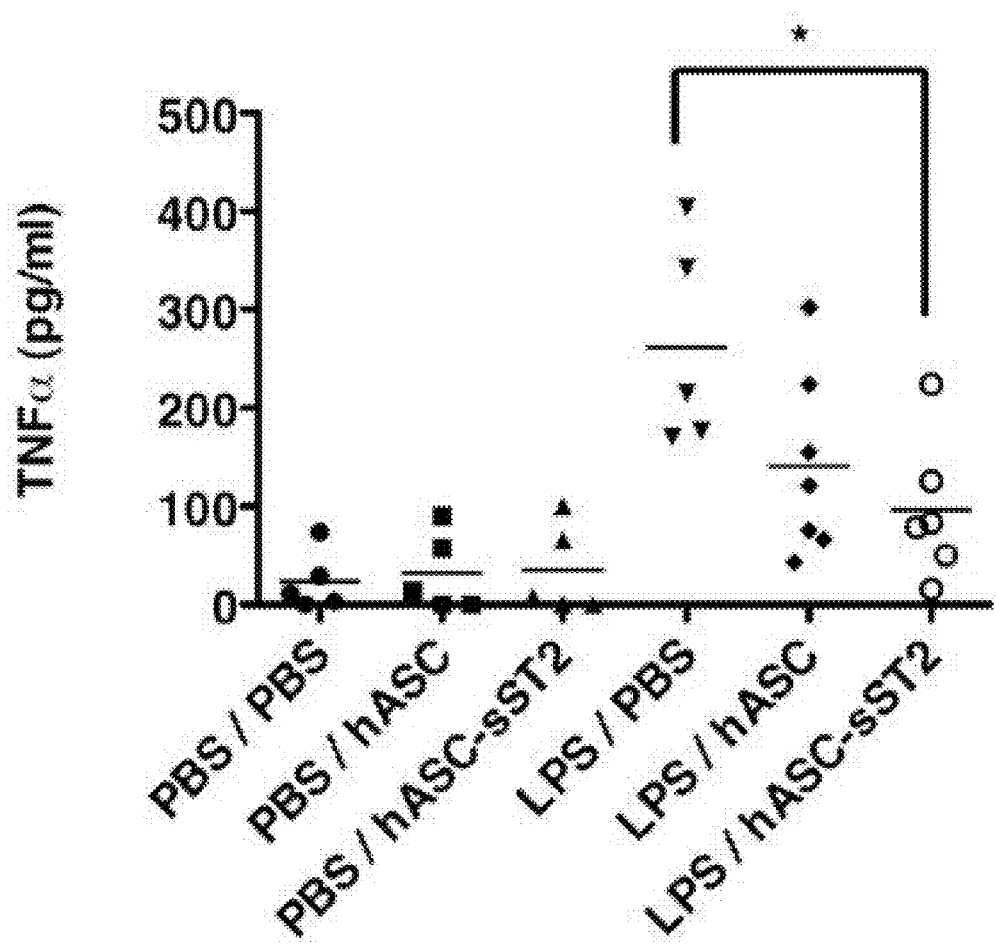
FIG. 9. BALF pro-inflammatory cytokine/chemokine levels after LPS-induced lung inflammation in mice. Levels of the pro-inflammatory cytokines TNF-α (A) and IL-6 (B), and of the chemokine MIP-2 (C) were measured at 48 h after LPS/PBS instillation through specific ELISAs. PBS/PBS, PBS-instilled, untreated mice; PBS/hASC, PBS-instilled, hASC-treated mice; LPS/PBS, LPS-induced, untreated mice; LPS/hASC, LPS-induced, hASC-treated mice; LPS/hASC-sST2, LPS-induced, hASC-sST2-treated mice (n=5-7 per group) (*p<0.05; p<0.01; *p<0.001 versus the LPS/PBS group).
Figure 9B:
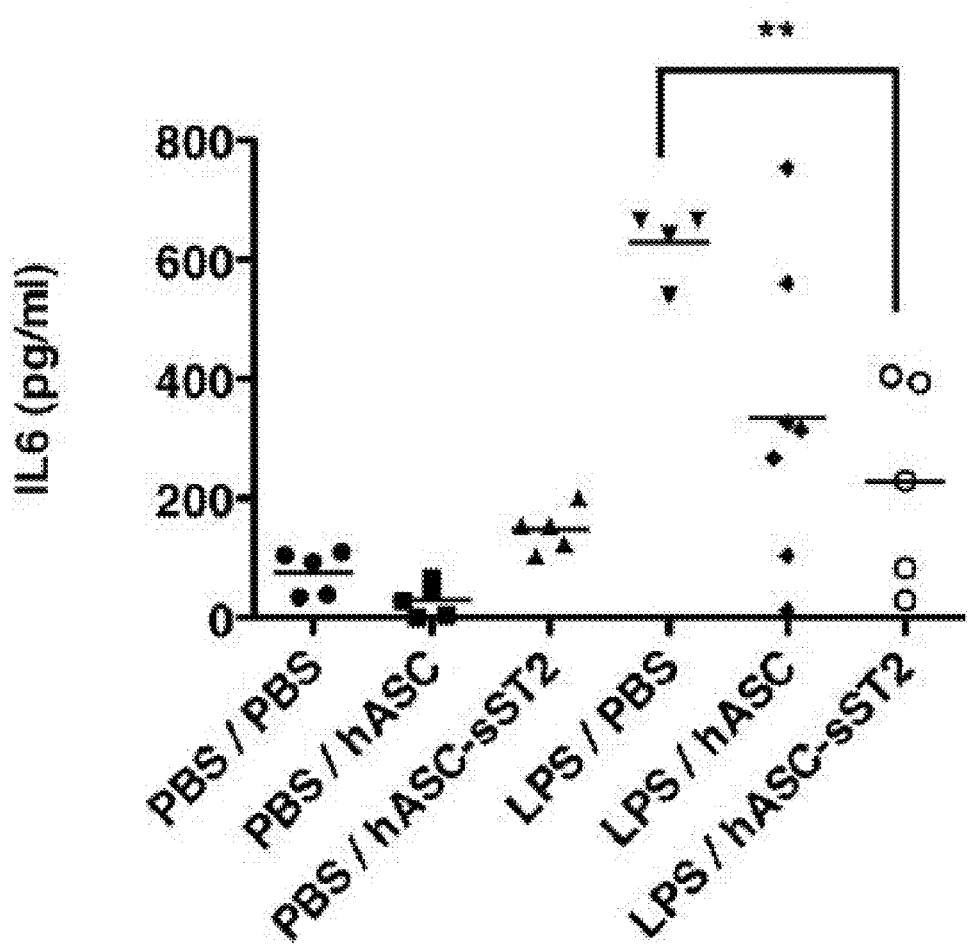
Figure 9C:
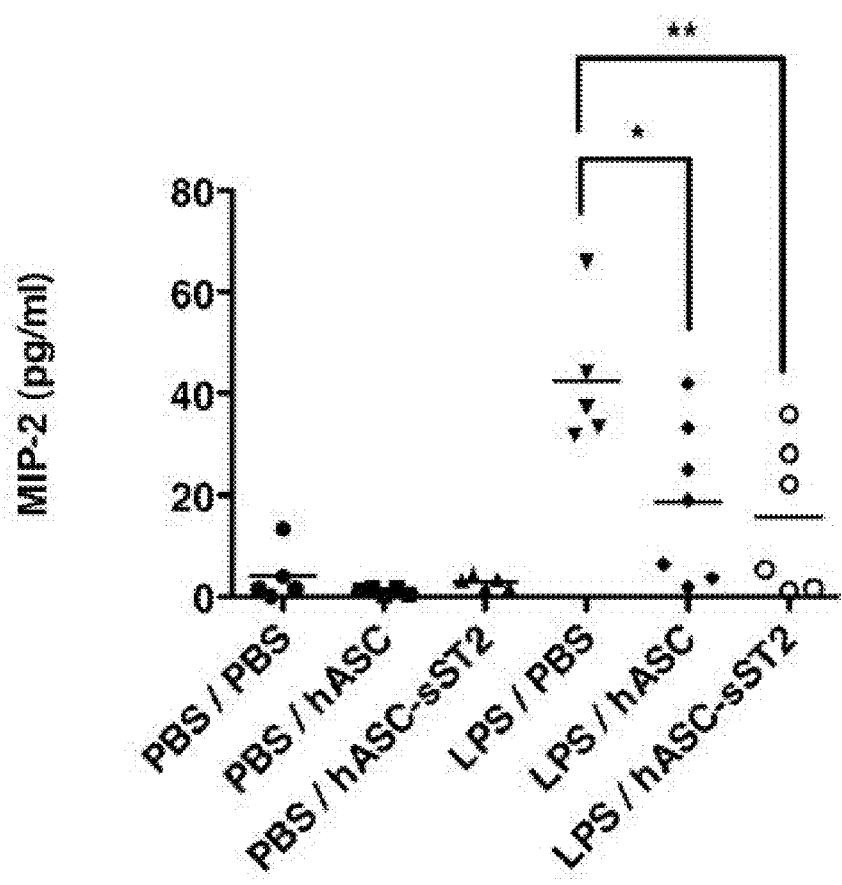

The levels of both the pro-inflammatory cytokines TNF-α and IL6, and the neutrophil chemoattractant MIP-2 are known to be actively involved in the pathophysiology of endotoxin-mediated pulmonary inflammation. Remarkably, all of them where found significantly reduced in the BALF of LPS-induced and hASC-sST2-treated mice, as compared with those present in LPS-induced and untreated mice. Moreover, hASC treatment after LPS-induction yielded intermediate BALF cytokine/chemokine levels (FIG. 9).

Figure 10A:
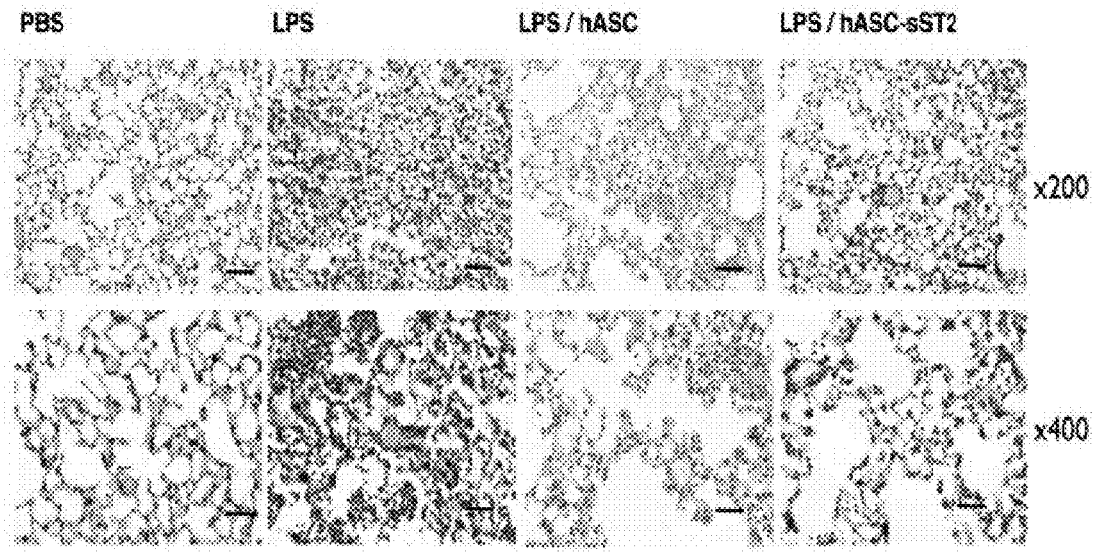
FIG. 10. Lung histopathology in the mouse ALI model. Histological evaluation of the therapeutic potential of hASC and hASC-sST2 on LPS-induced murine lung injury. Representative images of hematoxylin and eosin stained lung sections from control, PBS-instilled, untreated mice (PBS), LPS-induced, untreated mice (LPS), LPS-induced, hASC-treated mice (LPS/hASC), and LPS-induced, hASC-sST2-treated mice (LPS/hASC-sST2) at low (×200; upper panels) and high (×400; lower panels) magnification.
Figure 10B:
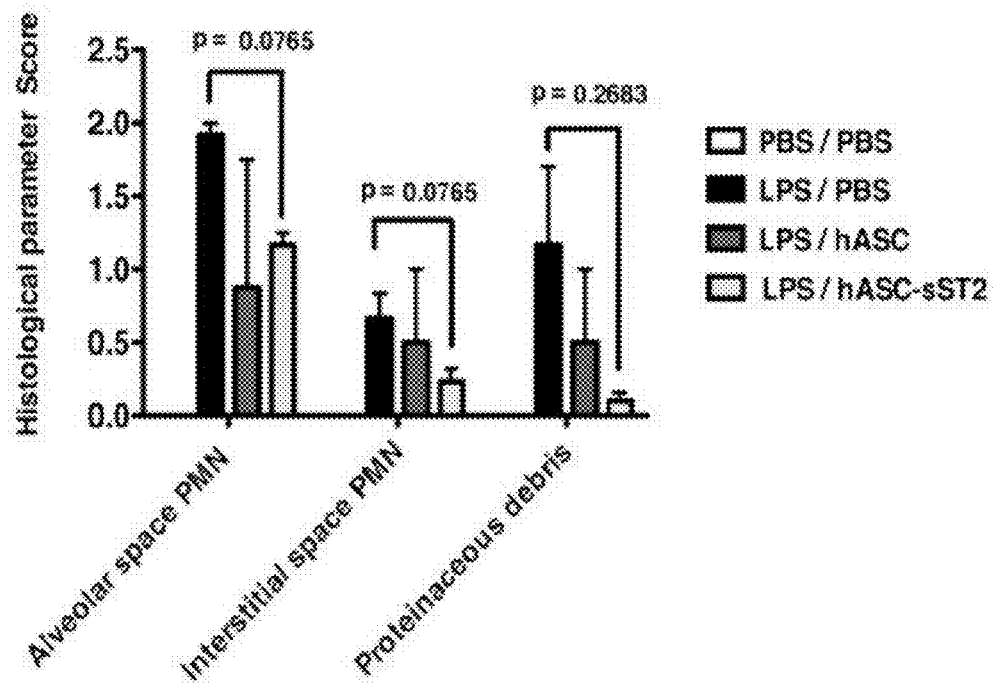

Next, a blinded histopathological examination of lung sections from the LPS-induced, untreated mice revealed a marked intra-alveolar inflammatory infiltrate consisting of polymorphonuclear leukocytes and macrophages at 48 h after endotoxin challenge, which was slightly reduced in LPS-induced and hASC-treated mice. In addition, hASC-sST2 treatment strikingly reduced the immune-inflammatory infiltrate present in LPS-challenged mice, leading to an improved histological appearance close to that from unchallenged control mice (see Table 1 and FIG. 10).

Figure 12A:
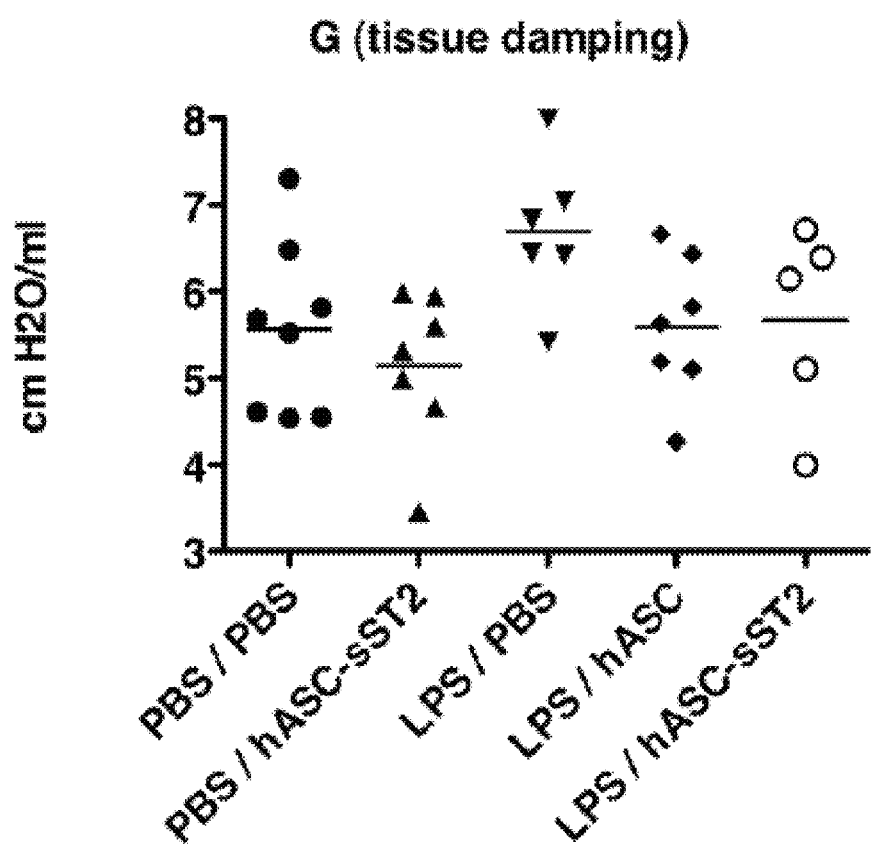
FIG. 12. Mechanical parameters of lung injury in the mouse ALI model. Lung function was determined at 48 h after PBS/LPS instillation using the forced oscillation technique and the constant phase model. (A) lung tissue damping; (B) lung tissue elastance. PBS/PBS, PBS-instilled, untreated mice; PBS/hASC, PBS-instilled, hASC-treated mice; LPS/PBS, LPS-induced, untreated mice; LPS/hASC, LPS-induced, hASC-treated mice; LPS/hASC-sST2, LPS-induced, hASC-sST2-treated mice (n=5-8 per group).
Figure 12B:
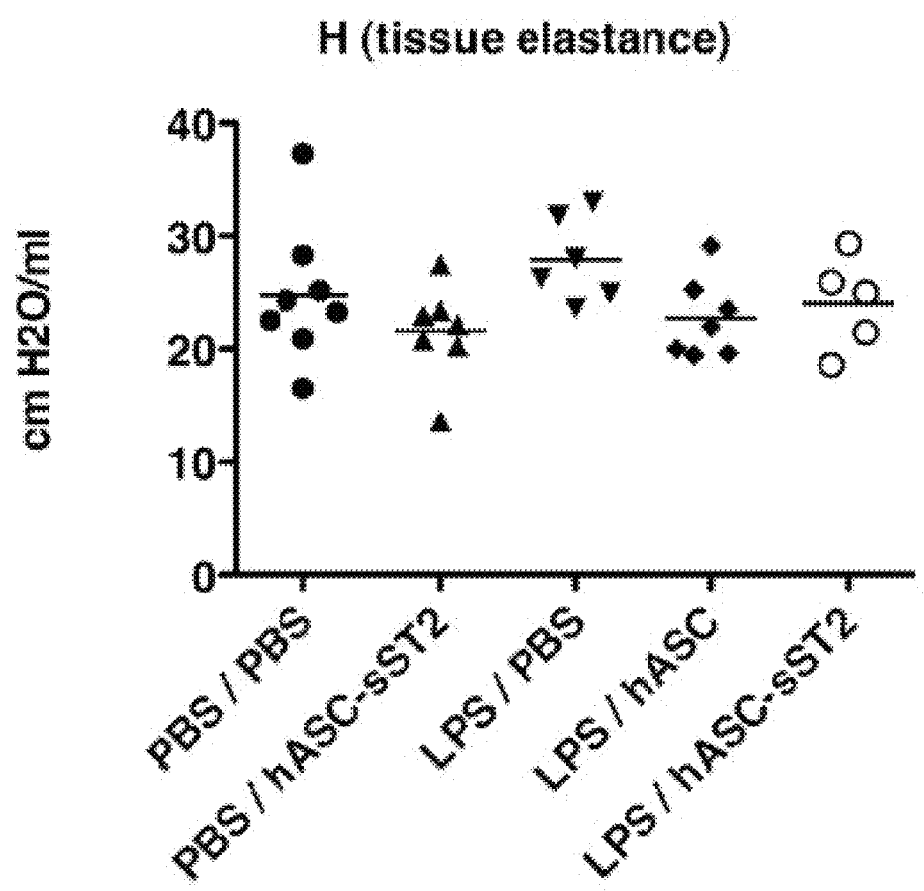

Finally, although our lung injury model was mainly designed to evaluate reversion of acute lung inflammation, we also attempted to quantify mechanical parameters from a pulmonary functional standpoint through forced oscillation mechanics. Thus at 48 h after endotoxin challenge, tissue damping or energy dissipation (G) and lung tissue elastance (H) tended to increase in LPS-induced mice compared with PBS-instilled control mice. In contrast, both mechanical parameters were reduced back to control levels in both hASC-treated and hASC-sST2-treated mice after LPS induction (FIG. 12).

TABLE 1

Histological parameter scoring in mice with LPS-induced ALI.

| Treatment | Alveolar space PMN | Interstitial space PMN | Proteinaceous debris |
|---|---|---|---|
| PBS/PBS | 0 | 0 | 0 |
| LPS/PBS | 1.91 ± 0.96 | 0.66 ± 0.40 | 1.16 ± 0.95 |
| LPS/hASC | 0.87 ± 1.01 | 0.50 ± 0.57 | 0.50 ± 0.57 |
| LPS/hASC-sST2 | 1.16 ± 0.59 | 0.23 ± 0.17 | 0.10 ± 0.09 |

Data are presented as mean ± standard deviation (PBS/PBS and LPS/hASC, n = 2; LPS/PBS and LPS/hASC-sST2, n = 3).

The invention claimed is:

1. Isolated Mesenchymal stem cells (MSC) genetically modified to express soluble ST2 (sST2) or functional variants thereof for use in the treatment of airway immune inflammatory and lung diseases.

2. The isolated mesenchymal stem cells for use in the treatment of airway immune inflammatory and lung diseases according to claim 1, comprising a vector containing nucleic acids that encode the expression of sST2 or functional variants thereof.

3. The isolated mesenchymal stem cells for use in the treatment of airway immune inflammatory and lung diseases according to claim 1, wherein said airway immune inflammatory and lung diseases are selected from acute lung injury, Chronic Obstructive Pulmonary Disease including chronic bronchitis, emphysema, bronchiectasis and bronchiolitis, acute respiratory distress syndrome, asthma, hypersensitivity pneumonitis and pulmonary fibrosis.

4. The isolated mesenchymal stem cells for use in the treatment of airway immune inflammatory and lung diseases according to claim 1, wherein said mesenchymal stem cells are in the form of single-cell suspensions, microcarriers or spheroids.

5. The isolated mesenchymal stem cells for use in the treatment of airway immune inflammatory and lung diseases according to claim 1, wherein the method used in said treatment comprises the administration of said mesenchymal stem cells by parenteral or pulmonary route of administration.

6. The isolated mesenchymal stem cells for use in the treatment of airway immune inflammatory and lung diseases according to claim 5, wherein said parenteral administration is via intravenous, intrapleural or intraarterial routes.

7. The isolated mesenchymal stem cells for use in the treatment of airway immune inflammatory and lung diseases according to claim 1, wherein said mesenchymal stem cells are obtained from adipose tissue.

8. A pharmaceutical composition for use in the treatment of airway immune inflammatory and lung diseases comprising the isolated mesenchymal stem cells according to claim 1.

* * * * *